United States Patent
Seow et al.

(10) Patent No.: US 10,233,445 B2
(45) Date of Patent: *Mar. 19, 2019

(54) COMPOSITION FOR DELIVERY OF GENETIC MATERIAL

(71) Applicant: Oxford University Innovation Limited, Oxford (GB)

(72) Inventors: Yiqi Seow, Singapore (SG); Lydia Alvarez, London (GB); Matthew Wood, Oxford (GB)

(73) Assignee: Oxford University Innovation Limited, Botley, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/847,853

(22) Filed: Sep. 8, 2015

(65) Prior Publication Data

US 2016/0067355 A1   Mar. 10, 2016

Related U.S. Application Data

(63) Continuation of application No. 13/264,485, filed as application No. PCT/GB2010/000762 on Apr. 15, 2010, now abandoned.

(30) Foreign Application Priority Data

Apr. 17, 2009   (GB) .................................. 0906692.9
Apr. 17, 2009   (GB) .................................. 0906693.7

(51) Int. Cl.

| | | |
|---|---|---|
| *C12N 15/11* | (2006.01) | |
| *C12N 15/113* | (2010.01) | |
| *A61K 48/00* | (2006.01) | |
| *A61K 47/42* | (2017.01) | |
| *C07K 7/06* | (2006.01) | |
| *C07K 14/005* | (2006.01) | |
| *C07K 14/435* | (2006.01) | |
| *C07K 14/705* | (2006.01) | |
| *A61K 47/69* | (2017.01) | |

(52) U.S. Cl.

CPC ............ *C12N 15/113* (2013.01); *A61K 47/42* (2013.01); *A61K 47/6901* (2017.08); *A61K 48/0025* (2013.01); *C07K 7/06* (2013.01); *C07K 14/005* (2013.01); *C07K 14/435* (2013.01); *C07K 14/705* (2013.01); *C12N 15/111* (2013.01); *A61K 48/00* (2013.01); *C07K 2319/035* (2013.01); *C12N 2310/14* (2013.01); *C12N 2310/315* (2013.01); *C12N 2320/32* (2013.01); *C12N 2760/20022* (2013.01); *C12N 2760/20031* (2013.01)

(58) Field of Classification Search

None
See application file for complete search history.

(56) References Cited

U.S. PATENT DOCUMENTS

| | | |
|---|---|---|
| 6,685,911 B1 | 2/2004 | Zitvogel et al. |
| 2002/0090374 A1* | 7/2002 | Yarkoni ................. C07K 14/55 424/178.1 |
| 2004/0024116 A1 | 2/2004 | Honnick |
| 2004/0028647 A1 | 2/2004 | Zagury et al. |
| 2004/0028692 A1 | 2/2004 | Zitvogel et al. |
| 2004/0197314 A1 | 10/2004 | Delcayre et al. |
| 2006/0222654 A1 | 10/2006 | Delcayre et al. |
| 2007/0298118 A1 | 12/2007 | Lotvall et al. |
| 2011/0177054 A1 | 7/2011 | Gibbings et al. |
| 2013/0053426 A1 | 2/2013 | Seow et al. |
| 2014/0356382 A1 | 12/2014 | Wood et al. |
| 2017/0182182 A1 | 6/2017 | Seow et al. |

FOREIGN PATENT DOCUMENTS

| | | | |
|---|---|---|---|
| AU | 2004203482 A1 | 8/2004 | |
| CN | 1325441 A | 12/2001 | |
| EP | 1537858 A1 * | 6/2005 | ........... A61K 9/1272 |
| JP | 2006518219 | 8/2006 | |
| WO | WO 1993/016522 A1 | 8/1993 | |
| WO | WO 1997/05900 A1 | 2/1997 | |
| WO | WO 2000/28001 A1 | 5/2000 | |
| WO | WO 0028001 A1 * | 5/2000 | ............ C07K 16/00 |
| WO | WO 2001/36601 A1 | 5/2001 | |
| WO | WO 2001/082958 A2 | 11/2001 | |
| WO | WO 2003/016522 A2 | 2/2003 | |
| WO | WO 2004/014954 A1 | 2/2004 | |
| WO | WO 2007/126386 A1 | 11/2007 | |
| WO | WO 2010/119256 A1 | 10/2010 | |
| WO | WO 2010/141716 A2 | 12/2010 | |
| WO | WO 2011/000511 A2 | 1/2011 | |

OTHER PUBLICATIONS

Zeng et al, A synthetic peptide containing loop 4 of nerve growth factor for targeted gene delivery, 2004, The Journal of Gene Medicine, 6: 1247-1256.*

Alvarez-Erviti, L., et al., "Delivery of siRNA to the Mouse Brain by Systemic Injection of Targeted Exosomes," *Nature Biotechnology*, 29(4): 341-347 (Apr. 2011).

Chen, S., et al., "Production of Specific CTL Induced by Exosomes Derived from K562 Cells," *Journal of Experimental Hematology*, 14(6): 1168-1171 (2006).

Delcayre & Le Pecq, "Exosomes as Novel Therapeutics Nanodevices," *Current Opinion in Mol. Ther.*, 8(1): 31-38 (2006).

Grosse, S., et al., "Potocytosis and Cellular Exit of Complexes as Cellular Pathways for Gene Delivery by Polycations," *Journal of Gene Medicine*, 7: 1275-1286 (2005).

(Continued)

*Primary Examiner* — Ekaterina Poliakova-Georgantas
(74) *Attorney, Agent, or Firm* — Hamilton, Brook, Smith & Reynolds, P.C.

(57) ABSTRACT

The present invention relates to exosomes, loaded with genetic material and methods of producing them and to the use of such exosomes for delivering genetic material in vivo, in particular the use of such exosomes in methods of gene therapy or gene silencing.

8 Claims, 17 Drawing Sheets

Specification includes a Sequence Listing.

(56) References Cited

OTHER PUBLICATIONS

Hao et al, "Cancer Immunotherapy by Exosome-Based Vaccines," Cancer Biother. Radiopharm., 22(5): 692-703 (2007).
International Preliminary Examination Report on Patentability for PCT/GB2010/000762, dated Oct. 18, 2011 for "Composition for Delivery of Genetic Material" (4 pages).
Luo et al, Mianyixue Zazhi 2003, 19, pp. 360-363 and CAPLUS Accession No. 2004:689681—Abstract only.
Luo et al, Shijie Huaren Xiaohua Zazhi 2004, 12, 9-12 and CAPLUS Accession No. 2005:24680—Abstract only.
Multiporator Basic Applications Manual, Eppendorf, pp. 27-50 (2006).
Notification of Transmittal of the International Search Report and Written Opinion of the International Searching Authority from counterpart International Application No. PCT/GB2010/000762, dated Aug. 2, 2010.
Quah, B., et al., "The immunogenicity of Dendritic Cell-Derived Exosomes," *Blood Cells, Molecules, and Diseases*, 35:94-110 (2005).
Raposo et al, "B Lymphocytes Secrete Antigen-presenting Vesicles," *J. Ex. Med.*, 183: 1161-1172 (1996).
Simhardri, V.R., et al., "Dendritic Cells Release HLA-B-Associated Transcript-3 Positive Exosomes to Regulate Natural Killer Function", PLOS One, 3(10):e3377, 8 pages (2008).
Skog, J., et al., "Glioblastoma microvesicles transport RNA and proteins that promote tumour growth and provide diagnostic biomarkers", *Nature Cell Biology*, 10: 1470-1476 (Dec. 2008).
United Kingdom Search Report for GB 0906692.9: Date of Search Aug. 13, 2009 (2 pgs.).
United Kingdom Search Report for GB 0906693.7: Date of Search Aug. 13, 2009 (2 pgs.).
Valadi, H., et al., "Exosome-mediated transfer of mRNAs and microRNAs is a novel mechanism of genetic exchange between cells", *Nature Cell Biology*, 9: 654-659 (Jun. 2007).
Zitvogel et al, "Eradication of Established Murine Tumors Using a Novel Cell-free Vaccine: Dendritic Cell-derived Exosomes," *Nat. Med.*, 4: 594-600 (1998).
Cho, I.S., et al., "Improved Serum Stability and Biophysical Properties of siRNAs Following Chemical Modifications," *Biotechnol. Lett.*, 30:1901-1908 (2008).
Temchura, V.V., et al., "Enhancement of Immunostimulatory Properties of Exosomal Vaccines by Incorporation of Fusion-Competent G Protein of Vesicular Stomatitis Virus," *Vaccine*, 26:3662-3672 (2008).
Altschul, S.F., "A Protein Alignment Scoring System Sensitive at All Evolutionary Distances", J Mol Evol, 36: 290-300 (1993).
Altschul, S.F., et al., "Basic Local Alignment Search Tool", J Mol Biol., 215: 403-410 (1990).
Bio-Medicine, "Pharma Research Challenge", 2 pages downloaded on May 23, 2013 from URL: http://news.bio-medicine.org/?q=biology-technology/optimizing-electroporation-para.
Delcayre, A., et al., "Exosome Display Technology: Application to the Development of New Diagnostics and Therapeutics", Blood Cells, Molecules and Diseases, 35: 158-168 (2005).
Devereaux, J., et al., "A Comprehensive Set of Sequence Analysis Programs for the VAX", Nucleic Acids Research, 12(1): 387-395 (1984).
Gallagher, J., "Breakthrough in Delivering Drugs to the Brain", BBC News, 2 pages, downloaded on May 8, 2012 from URL: http://www.bbc.co.uk/news/health-12776222.
Henikoff, S. and Henikoff, J.G., "Amino Acid Substitution Matrices from Protein Blocks", Proc. Natl. Acad. Sci., 89: 10915-10919 (1992).
International Preliminary Report on Patentability for PCT/GB2012/053052, "Exosomes for Delivery of Biotherapeutics" date of issuance Jun. 10, 2014.
Karlin, S. and Altschul, S.F., "Applications and Statistics for Multiple High-Scoring Segments in Molecular Sequences", Proc. Natl. Acad. Sci., 90: 5873-5877 (1993).
Mendonça, L.S., et al., "Transferrin Receptor-Targeted Liposomes Encapsulating Anti-BCR-ABL siRNA or asODN for Chronic Myeloid Leukemia Treatment", Bioconjugate Chem., 21:157-168 (2010).
Morgan, W.F. and Day, J.P., "The Introduction of Proteins into Mammalian Cells by Electroporation" in Methods in Molecular Biology, J.A. Nickoloff ed. (NJ: Humana Press, Inc), pp. 63-71 (1995).
Non-Final Office Action for U.S. Appl. No. 14/363,685, "Exosomes for Delivery of Biotherapeutics", dated May 9, 2017.
Notification of Transmittal of the International Search Report and the Written Opinion of the International Search Authority for PCT/GB2012/053052, "Exosomes for Delivery of Biotherapeutics" dated Aug. 6, 2013.
Qazi, K.R., et al., "Antigen-Loaded Exosomes Alone Induce Th1-Type Memory Through a B Cell-Dependent Mechanism", Blood, 113(12):2673-2683 (2009).
University of Oxford, Media web-page article, "New Method Delivers Alzheimers Drug to the Brain", updated Mar. 21, 2011, 4 pages, no author given, downloaded from URL: www.ox.ac.uk/media/new_stories/2011/112103.html.
Bader AG, et al "Developing therapeutic microRNAs for cancer" Gene Ther. 2011 18(12):1121-6; published Jun. 2, 2011.
Chakrabarty et al "Transfer of monoclonal antibodies into mammalian cells by electroporation" J Biol Chem. 1989; 264(26):15494-500; published Sep. 15, 1989.
Editorial (Ponsaerts and Berneman), "Modulation of cellular behavior by exogenous messenger RNA," Leukaemia, 20, 767-769; published May 1, 2006.
Holliger P & Hudson PJ "Engineered antibody fragments and the rise of single domains" Nat Biotechnol. 2005 ;23(9):1126-36; published Sep. 7, 2005.
Logozzi ,et al "High Levels of Exosomes Expressing CD63 and Caveolin-1 in Plasma of Melanoma Patients" PLoS One, vol. 4, No. 4, e5219, 10 pages, published Apr. 2009.
Ratacjzak et al., "Embryonic stem cell-derived microvesicles reprogram hematopoietic progenitors: evidence for horizontal transfer of mRNA and protein delivery," Leukaemia, 20, 847-856; published Feb. 2, 2006.
Non-Final Office Action for U.S. Appl. No. 15/364,794, "Composition for Delivery of Genetic Material", dated Aug. 25, 2017.
Final Office Action for U.S. Appl. No. 14/363,685, "Exosomes for Delivery of Biotherapeutics", dated Nov. 3, 2017.

\* cited by examiner

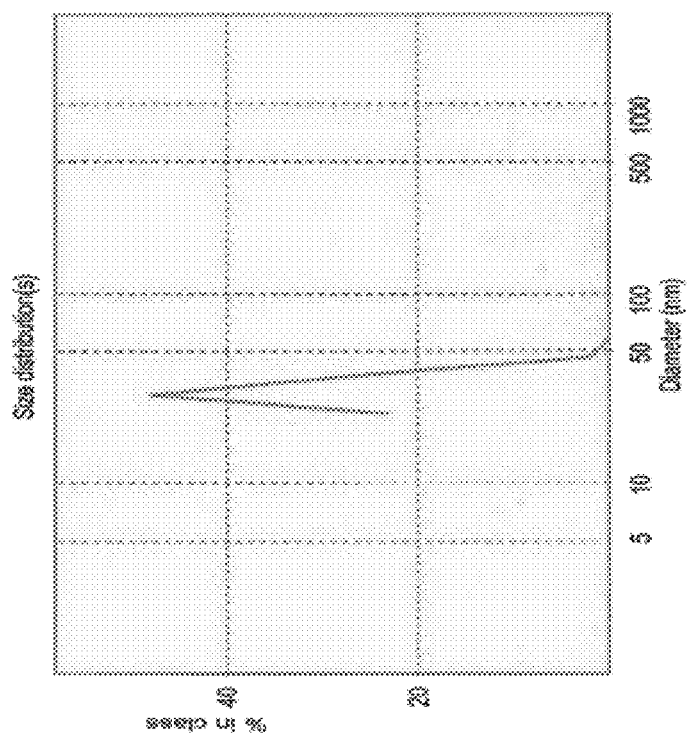
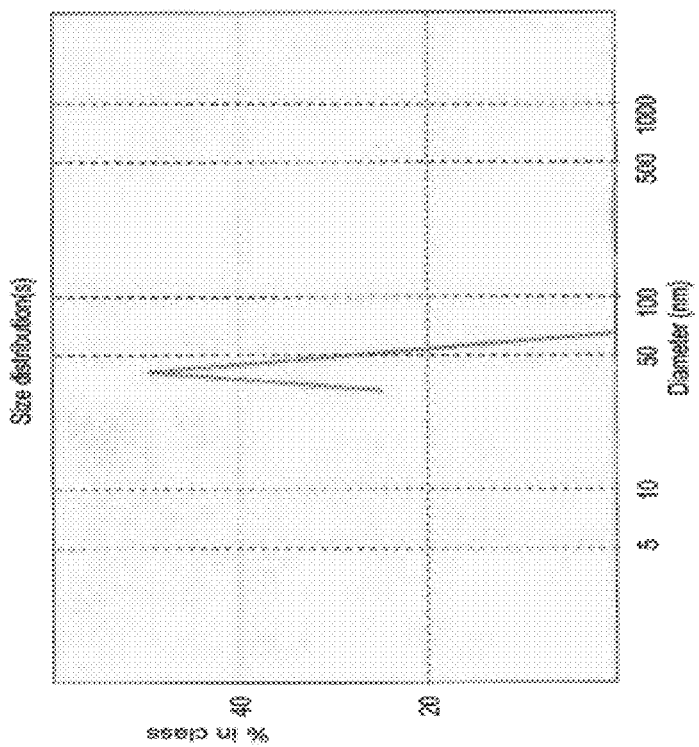
FIG 1C continue

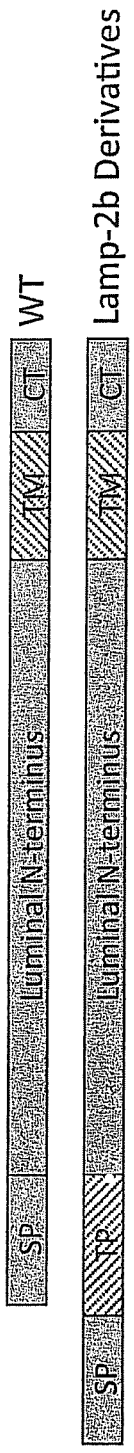
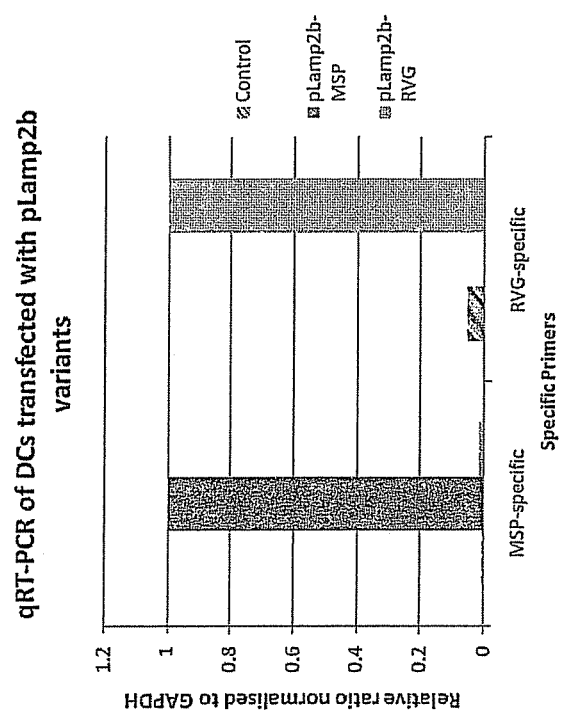
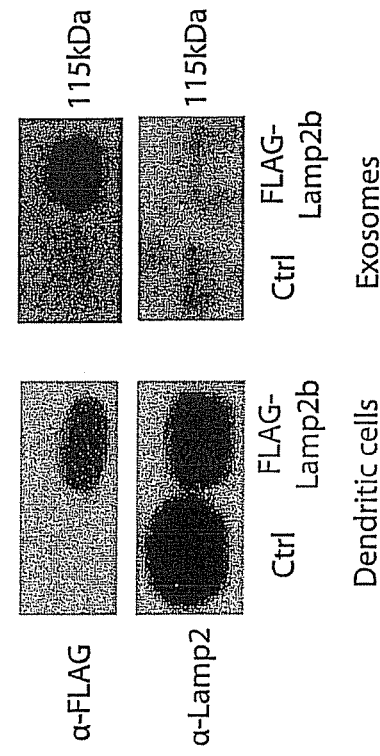
FIG. 2A
FIG. 2B
FIG. 2C

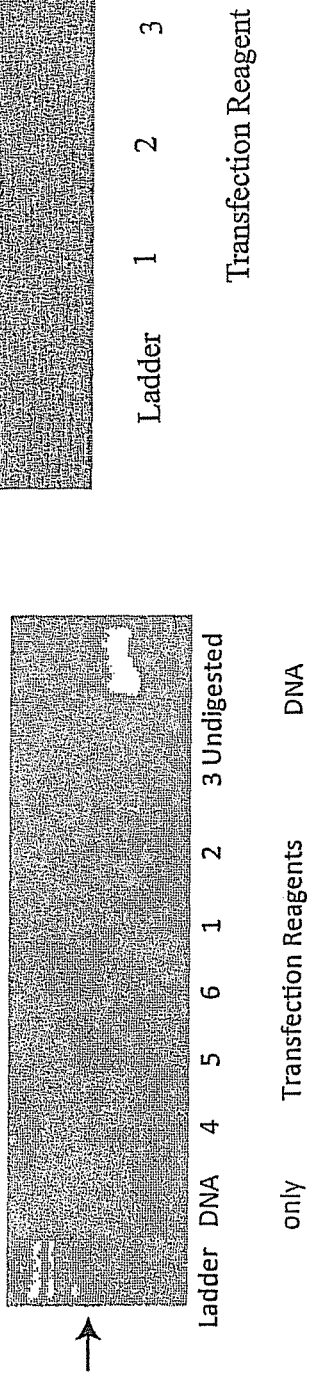
FIG. 3B
FIG. 3C
FIG. 3D

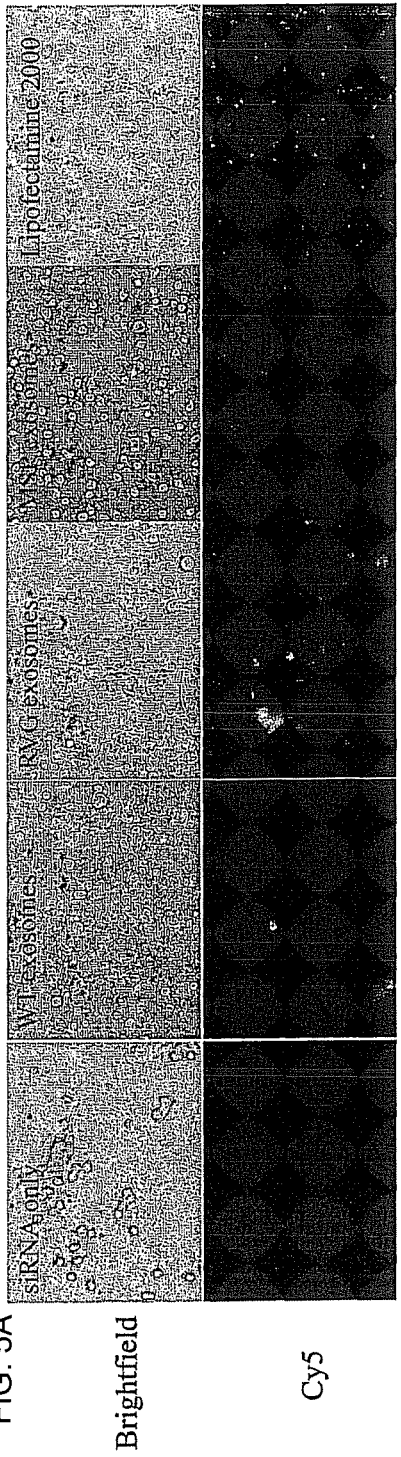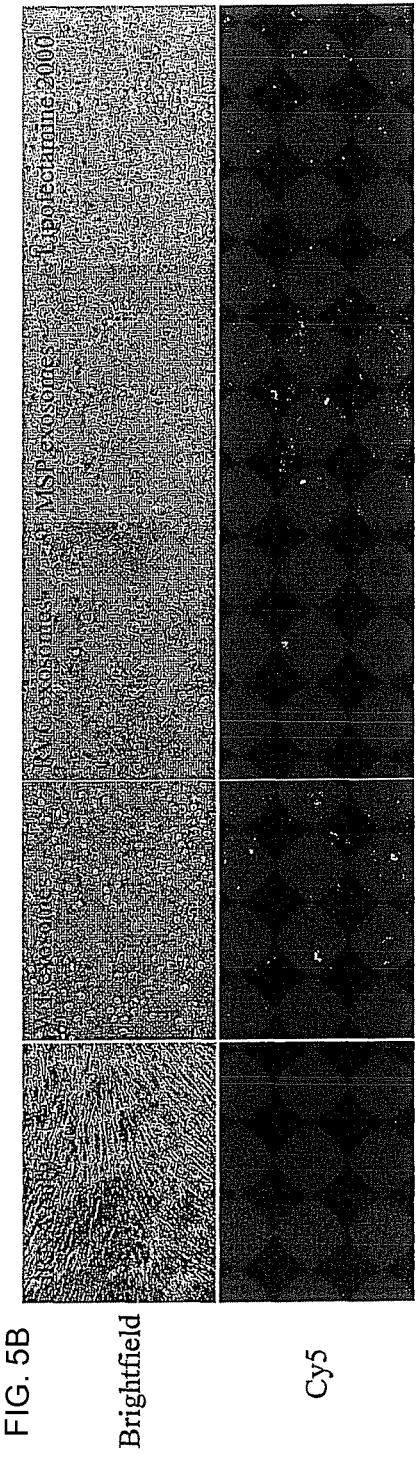

SEQUENCE LISTING

```
<160> NUMBER OF SEQ ID NOS: 25

<210> SEQ ID NO 1
<211> LENGTH: 415
<212> TYPE: PRT
<213> ORGANISM: Mus musculus

<400> SEQUENCE: 1

Met Cys Leu Ser Pro Val Lys Gly Ala Lys Leu Ile Leu Ile Phe Leu
1               5                   10                  15

Phe Leu Gly Ala Val Gln Ser Asn Ala Leu Ile Val Asn Leu Thr Asp
            20                  25                  30

Ser Lys Gly Thr Cys Leu Tyr Ala Glu Trp Glu Met Asn Phe Thr Ile
        35                  40                  45

Thr Tyr Glu Thr Thr Asn Gln Thr Asn Lys Thr Ile Thr Ile Ala Val
    50                  55                  60

Pro Asp Lys Ala Thr His Asp Gly Ser Ser Cys Gly Asp Asp Arg Asn
65                  70                  75                  80

Ser Ala Lys Ile Met Ile Gln Phe Gly Phe Ala Val Ser Trp Ala Val
                85                  90                  95

Asn Phe Thr Lys Glu Ala Ser His Tyr Ser Ile His Asp Ile Val Leu
            100                 105                 110

Ser Tyr Asn Thr Ser Asp Ser Thr Val Phe Pro Gly Ala Val Ala Lys
        115                 120                 125

Gly Val His Thr Val Lys Asn Pro Glu Asn Phe Lys Val Pro Leu Asp
    130                 135                 140

Val Ile Phe Lys Cys Asn Ser Val Leu Thr Tyr Asn Leu Thr Pro Val
```

```
                145                 150                 155                 160
    Val Gln Lys Tyr Trp Gly Ile His Leu Gln Ala Phe Val Gln Asn Gly
                    165                 170                 175
    Thr Val Ser Lys Asn Glu Gln Val Cys Glu Glu Asp Gln Thr Pro Thr
                    180                 185                 190
    Thr Val Ala Pro Ile Ile His Thr Thr Ala Pro Ser Thr Thr Thr Thr
                    195                 200                 205
    Leu Thr Pro Thr Ser Thr Pro Thr Pro Thr Pro Thr Pro Thr Pro Thr
                210                 215                 220
    Val Gly Asn Tyr Ser Ile Arg Asn Gly Asn Thr Thr Cys Leu Leu Ala
    225                 230                 235                 240
    Thr Met Gly Leu Gln Leu Asn Ile Thr Glu Glu Lys Val Pro Phe Ile
                        245                 250                 255
    Phe Asn Ile Asn Pro Ala Thr Thr Asn Phe Thr Gly Ser Cys Gln Pro
                        260                 265                 270
    Gln Ser Ala Gln Leu Arg Leu Asn Asn Ser Gln Ile Lys Tyr Leu Asp
                    275                 280                 285
    Phe Ile Phe Ala Val Lys Asn Glu Lys Arg Phe Tyr Leu Lys Glu Val
                290                 295                 300
    Asn Val Tyr Met Tyr Leu Ala Asn Gly Ser Ala Phe Asn Ile Ser Asn
    305                 310                 315                 320
    Lys Asn Leu Ser Phe Trp Asp Ala Pro Leu Gly Ser Ser Tyr Met Cys
                        325                 330                 335
    Asn Lys Glu Gln Val Leu Ser Val Ser Arg Ala Phe Gln Ile Asn Thr
                    340                 345                 350
    Phe Asn Leu Lys Val Gln Pro Phe Asn Val Thr Lys Gly Gln Tyr Ser
                    355                 360                 365
    Thr Ala Gln Glu Cys Ser Leu Asp Asp Asp Thr Ile Leu Ile Pro Ile
                370                 375                 380
    Ile Val Gly Ala Gly Leu Ser Gly Leu Ile Ile Val Ile Val Ile Ala
    385                 390                 395                 400
    Tyr Leu Ile Gly Arg Arg Lys Thr Tyr Ala Gly Tyr Gln Thr Leu
                        405                 410                 415

<210> SEQ ID NO 2
<211> LENGTH: 1248
<212> TYPE: DNA
<213> ORGANISM: Mus musculus

<400> SEQUENCE: 2
atgtgcctct ctccggttaa aggcgcaaag ctcatcctga tctttctgtt cctaggagcc      60
gttcagtcca atgcattgat agttaatttg acagattcaa agggtacttg cctttatgca     120
gaatgggaga tgaatttcac aataacatat gaaactacaa accaaaccaa taaaactata     180
accattgcag tacctgacaa ggcgacacac gatggaagca gttgtgggga tgaccggaat     240
agtgccaaaa taatgataca atttggattc gctgtctctt gggctgtgaa ttttaccaag     300
gaagcatctc attattcaat tcatgacatc gtgctttcct acaacactag tgatagcaca     360
gtatttcctg gtgctgtagc taaaggagtt catactgtta aaaatcctga aatttcaaa      420 gttccattgg atgtcatctt taagtgcaat agtgttttaa cttacaacct gactcctgtc     480
gttcagaaat attggggtat tcacctgcaa gcttttgtcc aaaatggtac agtgagtaaa     540
aatgaacaag tgtgtgaaga agaccaaact cccaccactg tggcacccat cattcacacc     600 actgcccccgt cgactacaac tacactcact ccaacttcaa cacccactcc aactccaact     660
```

```
ccaactccaa ccgttggaaa ctacagcatt agaaatggca atactacctg tctgctggct    720
accatggggc tgcagctgaa catcactgag gagaaggtgc ctttcatttt taacatcaac    780
cctgccacaa ccaacttcac cggcagctgt caacctcaaa gtgctcaact taggctgaac    840
aacagccaaa ttaagtatct tgactttatc tttgctgtga aaaatgaaaa acggttctat    900
ctgaaggaag tgaatgtcta catgtatttg gctaatggct cagctttcaa catttccaac    960
aagaacctta gcttctggga tgcccctctg gaagttctt atatgtgcaa caaagagcag   1020
gtgctttctg tgtctagagc gtttcagatc aacacccttta acctaaaggt gcaaccttt   1080 aatgtgacaa aaggacagta ttctacagcc caggagtgtt cgctggatga tgacaccatt   1140
ctaataccaa ttatagttgg tgctggtctt tcaggcttga ttatcgttat agtgattgct   1200
tacctaattg gcagaagaaa gacctatgct ggatatcaga ctctgtaa              1248
```

<210> SEQ ID NO 3
<211> LENGTH: 40
<212> TYPE: PRT
<213> ORGANISM: Artificial Sequence
<220> FEATURE:
<223> OTHER INFORMATION: Fragment of modified amino acid sequence of
      murine Lamp 2 isoform 2: N-terminal to peptide tag

<400> SEQUENCE: 3

Met Cys Leu Ser Pro Val Lys Gly Ala Lys Leu Ile Leu Ile Phe Leu
 1               5                  10                  15

Phe Leu Gly Ala Val Gln Ser Asn Ala Leu Ile Val Asn Leu Thr Asp
            20                  25                  30

Ser Lys Gly Thr Cys Leu Tyr Ala
        35                  40

<210> SEQ ID NO 4
<211> LENGTH: 378
<212> TYPE: PRT
<213> ORGANISM: Artificial Sequence
<220> FEATURE:
<223> OTHER INFORMATION: Fragment of modified amino acid sequence of
      murine Lamp 2 isoform 2: C-terminal to peptide tag
<400> SEQUENCE: 4

Gly Gly Ala Glu Trp Glu Met Asn Phe Thr Ile Thr Tyr Glu Thr Thr
 1               5                  10                  15

Asn Gln Thr Asn Lys Thr Ile Thr Ile Ala Val Pro Asp Lys Ala Thr
            20                  25                  30

His Asp Gly Ser Ser Cys Gly Asp Asp Arg Asn Ser Ala Lys Ile Met
        35                  40                  45

Ile Gln Phe Gly Phe Ala Val Ser Trp Ala Val Asn Phe Thr Lys Glu
    50                  55                  60

Ala Ser His Tyr Ser Ile His Asp Ile Val Leu Ser Tyr Asn Thr Ser
65                  70                  75                  80

Asp Ser Thr Val Phe Pro Gly Ala Val Ala Lys Gly Val His Thr Val
                85                  90                  95

Lys Asn Pro Glu Asn Phe Lys Val Pro Leu Asp Val Ile Phe Lys Cys
            100                 105                 110

Asn Ser Val Leu Thr Tyr Asn Leu Thr Pro Val Val Gln Lys Tyr Trp
        115                 120                 125

Gly Ile His Leu Gln Ala Phe Val Gln Asn Gly Thr Val Ser Lys Asn
    130                 135                 140

Glu Gln Val Cys Glu Glu Asp Gln Thr Pro Thr Thr Val Ala Pro Ile

```
                145                 150                 155                 160
        Ile His Thr Thr Ala Pro Ser Thr Thr Thr Thr Leu Thr Pro Thr Ser
                        165                 170                 175
        Thr Pro Thr Pro Thr Pro Thr Pro Thr Pro Thr Val Gly Asn Tyr Ser
                        180                 185                 190
        Ile Arg Asn Gly Asn Thr Thr Cys Leu Leu Ala Thr Met Gly Leu Gln
                        195                 200                 205
        Leu Asn Ile Thr Glu Glu Lys Val Pro Phe Ile Phe Asn Ile Asn Pro
                210                 215                 220
        Ala Thr Thr Asn Phe Thr Gly Ser Cys Gln Pro Gln Ser Ala Gln Leu
        225                 230                 235                 240
        Arg Leu Asn Asn Ser Gln Ile Lys Tyr Leu Asp Phe Ile Phe Ala Val
                        245                 250                 255
        Lys Asn Glu Lys Arg Phe Tyr Leu Lys Glu Val Asn Val Tyr Met Tyr
                        260                 265                 270
        Leu Ala Asn Gly Ser Ala Phe Asn Ile Ser Asn Lys Asn Leu Ser Phe
                        275                 280                 285
        Trp Asp Ala Pro Leu Gly Ser Ser Tyr Met Cys Asn Lys Glu Gln Val
                290                 295                 300
        Leu Ser Val Ser Arg Ala Phe Gln Ile Asn Thr Phe Asn Leu Lys Val
        305                 310                 315                 320
        Gln Pro Phe Asn Val Thr Lys Gly Gln Tyr Ser Thr Ala Gln Glu Cys
                        325                 330                 335
        Ser Leu Asp Asp Asp Thr Ile Leu Ile Pro Ile Ile Val Gly Ala Gly
                        340                 345                 350
        Leu Ser Gly Leu Ile Ile Val Ile Val Ile Ala Tyr Leu Ile Gly Arg
                        355                 360                 365
        Arg Lys Thr Tyr Ala Gly Tyr Gln Thr Leu
                        370                 375

<210> SEQ ID NO 5
<211> LENGTH: 1270
<212> TYPE: DNA
<213> ORGANISM: Artificial Sequence
<220> FEATURE:
<223> OTHER INFORMATION: Modified nucleotide sequence of murine Lamp 2
      isoform 2

<400> SEQUENCE: 5
atgtgcctct ctccggttaa aggcgcaaag ctcatcctga tctttctgtt cctaggagcc      60
gttcagtcca atgcattgat agttaatttg acagattcaa agggtacttg cctttatgct     120
cgaggtcaca tccggaggtg cagaatggga gatgaatttc acaataacat atgaaactac     180
aaaccaaacc aataaaacta taaccattgc agtacctgac aaggcgacac acgatggaag     240
cagttgtggg gatgaccgga atagtgccaa ataatgata caatttggat tcgctgtctc      300
ttgggctgtg aatttttacca aggaagcatc tcattattca attcatgaca tcgtgctttc     360
ctacaacact agtgatagca cagtatttcc tggtgctgta gctaaggag ttcatactgt      420 taaaaatcct gagaatttca agttccatt ggatgtcatc tttaagtgca atagtgtttt      480
aacttacaac ctgactcctg tcgttcagaa atattggggt attcacctgc aagcttttgt     540
ccaaaatggt acagtgagta aaaatgaaca agtgtgtgaa gagaccaaa ctcccaccac      600 tgtggcaccc atcattcaca ccactgcccc gtcgactaca actacactca ctccaacttc     660
aacacccact ccaactccaa ctccaactcc aaccgttgga aactacagca ttagaaatgg     720
```

```
caatactacc tgtctgctgg ctaccatggg gctgcagctg aacatcactg aggagaaggt    780
gcctttcatt tttaacatca accctgccac aaccaacttc accggcagct gtcaacctca    840
aagtgctcaa cttaggctga acaacagcca aattaagtat cttgacttta tctttgctgt    900
gaaaaatgaa aaacggttct atctgaagga agtgaatgtc tacatgtatt tggctaatgg    960
ctcagctttc aacatttcca acaagaacct tagcttctgg gatgcccctc tgggaagttc   1020
ttatatgtgc aacaaagagc aggtgctttc tgtgtctaga gcgtttcaga tcaacacctt   1080
taacctaaag gtgcaacctt ttaatgtgac aaaaggacag tattctacag cccaggagtg   1140
ttcgctggat gatgcacca ttctaatacc aattatagtt ggtgctggtc tttcaggctt    1200
gattatcgtt atagtgattg cttacctaat tggcagaaga aagacctatg ctggatatca   1260
gactctgtaa                                                          1270
```

<210> SEQ ID NO 6
<211> LENGTH: 29
<212> TYPE: PRT
<213> ORGANISM: Artificial Sequence
<220> FEATURE:
<223> OTHER INFORMATION: neuron-specific rabies viral glycoprotein (RVG)

<400> SEQUENCE: 6

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 7
<211> LENGTH: 92
<212> TYPE: DNA
<213> ORGANISM: Artificial Sequence
<220> FEATURE:
<223> OTHER INFORMATION: RVG forward primer

<400> SEQUENCE: 7
tcgatacacc atttggatgc ccgagaatcc gagaccaggg acaccttgtg acattttac     60 caatagcaga gggaagagag catccaacgg gt                                  92

<210> SEQ ID NO 8
<211> LENGTH: 92
<212> TYPE: DNA
<213> ORGANISM: Artificial Sequence
<220> FEATURE:
<223> OTHER INFORMATION: RVG reverse primer

<400> SEQUENCE: 8
ccggacccgt tggatgctct cttccctctg ctattggtaa aaatgtcaca aggtgtccct     60
ggtctcggat tctcgggcat ccaaatggtg ta                                  92

<210> SEQ ID NO 9
<211> LENGTH: 7
<212> TYPE: PRT
<213> ORGANISM: Artificial Sequence
<220> FEATURE:
<223> OTHER INFORMATION: muscle-specific peptide (MSP) identified by in
      vivo phage display

<400> SEQUENCE: 9

Ala Ser Ser Leu Asn Ile Ala
1               5

-continued

```
<210> SEQ ID NO 10
<211> LENGTH: 26
<212> TYPE: DNA
<213> ORGANISM: Artificial Sequence
<220> FEATURE:
<223> OTHER INFORMATION: MSP forward primer

<400> SEQUENCE: 10
tcgagccagc agcctgaaca tcgcct                                          26

<210> SEQ ID NO 11
<211> LENGTH: 26
<212> TYPE: DNA
<213> ORGANISM: Artificial Sequence
<220> FEATURE:
<223> OTHER INFORMATION: MSP reverse primer

<400> SEQUENCE: 11
ccggaggcga tgttcaggct gctggc                                          26

<210> SEQ ID NO 12
<211> LENGTH: 8
<212> TYPE: PRT
<213> ORGANISM: Artificial Sequence
<220> FEATURE:
<223> OTHER INFORMATION: FLAG

<400> SEQUENCE: 12

Asp Tyr Lys Asp Asp Asp Asp Lys
 1               5

<210> SEQ ID NO 13
<211> LENGTH: 29
<212> TYPE: DNA
<213> ORGANISM: Artificial Sequence
<220> FEATURE:
<223> OTHER INFORMATION: FLAG forward primer

<400> SEQUENCE: 13
tcgagattac aaggatgacg atgacaagt                                       29

<210> SEQ ID NO 14
<211> LENGTH: 29
<212> TYPE: DNA
<213> ORGANISM: Artificial Sequence
<220> FEATURE:
<223> OTHER INFORMATION: FLAG reverse primer

<400> SEQUENCE: 14
ccggacttgt catcgtcatc cttgtaatc                                       29

<210> SEQ ID NO 15
<211> LENGTH: 23
<212> TYPE: DNA
<213> ORGANISM: Artificial Sequence
<220> FEATURE:
<223> OTHER INFORMATION: Cyclophilin-B human forward primer

<400> SEQUENCE: 15
aaagtcaccg tcaaggtgta ttt                                             23

<210> SEQ ID NO 16
<211> LENGTH: 22
<212> TYPE: DNA
<213> ORGANISM: Artificial Sequence
<220> FEATURE:
<223> OTHER INFORMATION: Cyclophilin-B human reverse primer
```

<400> SEQUENCE: 16
tcaccgtaga tgctctttcc tc                                                 22

<210> SEQ ID NO 17
<211> LENGTH: 20
<212> TYPE: DNA
<213> ORGANISM: Artificial Sequence
<220> FEATURE:
<223> OTHER INFORMATION: GAPDH human forward primer

<400> SEQUENCE: 17
aaggtgaagg tcggagtcaa                                                    20

<210> SEQ ID NO 18
<211> LENGTH: 20
<212> TYPE: DNA
<213> ORGANISM: Artificial Sequence
<220> FEATURE:
<223> OTHER INFORMATION: GADPH human reverse primer

<400> SEQUENCE: 18
gaagatggtg atgggatttc                                                    20

<210> SEQ ID NO 19
<211> LENGTH: 21
<212> TYPE: DNA
<213> ORGANISM: Artificial Sequence
<220> FEATURE:
<223> OTHER INFORMATION: GAPDH mouse forward primer

<400> SEQUENCE: 19
caatgtgtcc gtcgtggatc t                                                  21

<210> SEQ ID NO 20
<211> LENGTH: 21
<212> TYPE: DNA
<213> ORGANISM: Artificial Sequence
<220> FEATURE:
<223> OTHER INFORMATION: GAPDH mouse reverse primer

<400> SEQUENCE: 20
tagcccaaga tgcccttcag t                                                  21

<210> SEQ ID NO 21
<211> LENGTH: 19
<212> TYPE: DNA
<213> ORGANISM: Artificial Sequence
<220> FEATURE:
<223> OTHER INFORMATION: eGFP forward primer

<400> SEQUENCE: 21
tcttcaagtc cgccatgcc                                                     19

<210> SEQ ID NO 22
<211> LENGTH: 19
<212> TYPE: DNA
<213> ORGANISM: Artificial Sequence
<220> FEATURE:
<223> OTHER INFORMATION: eGFP reverse primer

<400> SEQUENCE: 22
tgtcgccctc gaacttcac                                                     19

<210> SEQ ID NO 23

```
<211> LENGTH: 20
<212> TYPE: DNA
<213> ORGANISM: Artificial Sequence
<220> FEATURE:
<223> OTHER INFORMATION: 18s forward primer

<400> SEQUENCE: 23
gtaacccgtt gaaccccatt                                                    20

<210> SEQ ID NO 24
<211> LENGTH: 20
<212> TYPE: DNA
<213> ORGANISM: Artificial Sequence
<220> FEATURE:
<223> OTHER INFORMATION: 18s reverse primer

<400> SEQUENCE: 24
ccatccaatc ggtagtagcg                                                    20

<210> SEQ ID NO 25
<211> LENGTH: 245
<212> TYPE: DNA
<213> ORGANISM: Artificial Sequence
<220> FEATURE:
<223> OTHER INFORMATION: Unknown

<400> SEQUENCE: 25
atgtgcctct ctccggttaa aggcgcaaag ctcatcctga tctttctgtt cctaggagcc        60
gttcagtcca atgcattgat agttaatttg acagattcaa agggtacttg cctttatgct       120
cgaggtcaca tccggaggtg cagaatggga gatgaatttc acaataacat atgaaactac       180
aaaccaaacc aataaaacta taaccattgc agtacctgac aaggcgacac acgatggaag       240
cagtt                                                                   245
```

COMPOSITION FOR DELIVERY OF GENETIC MATERIAL

RELATED APPLICATIONS

This application is a continuation of U.S. application Ser. No. 13/264,485, filed Apr. 15, 2010, which is the U.S. National Stage of International Application No. PCT/GB2010/000762, filed Apr. 15, 2010, which designates the U.S., published in English, and claims priority under 35 U.S.C. §§ 119 or 365(c) to GB Application No. 0906693.7, filed Apr. 17, 2009 and GB Application No. 0906692.9, filed Apr. 17, 2009. The entire teachings of the above application(s) are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
   a) File name: 47761000001SUBSTITUTESEQUENCELISTING.txt; created Sep. 28, 2016, 15 KB in size.

FIELD OF THE INVENTION

The present invention relates to compositions for the delivery of nucleic acid or genetic material. In particular the present invention relates to exosomes, loaded with genetic material and methods of producing them.

BACKGROUND OF THE INVENTION

Nucleic acids are routinely used in gene therapy for the replacement of non-functional genes [1] and for neutralization of disease-causing mutations via RNA interference (RNAi) effector molecules such as miRNAs [2], shRNAs [3] and siRNAs [4]. As naked DNA and RNA are difficult to deliver in vivo due to rapid clearance [5], nucleases [6], lack of organ-specific distribution and low efficacy of cellular uptake, specialized gene delivery vehicles are usually used for delivery.

Viral vectors and cationic liposomes are at the forefront of delivery vehicle technology and have been relatively successful with a large number of these delivery vehicles already in clinical trial [7]. Despite these successes, there remain significant limitations that restrict many applications, the most significant of which are immune recognition [8, 9, 10] for most viral vectors and mutagenic integration [11] for viruses such as lentiviruses; and inflammatory toxicity and rapid clearance for liposomes [12, 13, 14, 15]. Recognition by the innate immune system leads to acute inflammatory responses, which may require the use of immunosuppression strategies to overcome uptake and re-administration issues of current strategies [16, 17, 18] potentially exposing patients to unwarranted risks of opportunistic infections. Antibodies generated against the delivery vehicles also dramatically decrease transgene expression on subsequent administration [19].

The inherent risks and limitations of current strategies have generally limited them to life-threatening diseases of which the benefits of therapy clearly outweigh the risks, such as severe combined immunodeficiency [20], to diseases in special environments, such as immuno-privileged sites like the eye [1], or for genetic vaccination [21]. However, for genetic diseases which are chronic and debilitating but not life-threatening, such as myotonic dystrophy, a much lower risk profile and the ability to sustain corrective gene therapy for decades, not years, is required for curative intervention. An example of a potentially unacceptable risk for this class of diseases is immunosuppression strategies discussed above, highlighted by the death of a healthy patient in a recent AAV gene therapy trial for rheumatoid arthritis due to an opportunistic infection caused by immunosuppressants [22] taken by the subject unbeknownst to the trial administrators. With the increasing number of diseases shown to possess a genetic component, including obesity, heart disease and psychiatric illnesses, there is tremendous potential for the modification of susceptibility genes for preemptive genetic solutions, but only if the risks are further reduced and long-term sustainability is achieved. Hence, it is imperative to develop technologies that are able to avoid immune recognition and inflammation, while retaining good delivery efficiencies, in order to expand the use of gene therapy beyond lethal diseases.

One of the solutions may lie in the use of exosomes for gene delivery. Exosomes are small membrane-bound vesicles (30-100 nm) of endocytic origin that are released into the extracellular environment following fusion of multivesicular bodies with the plasma membrane. Exosome production has been described for many immune cells including B cells, T cells, and dendritic cells (DCs). Exosomes derived from B lymphocytes and mature DCs express MHC-II, MHC-I, CD86 and ICAM-1 [23, 24], and have been used to induce specific anti-tumor T cytotoxic responses and anti-tumor immunity in experimental models and clinical trials [24, 25]. The potential of exosome-mediated gene delivery has been shown with delivery of murine mRNAs and miRNAs to human mast cells [26] and glioma-derived exosomes [27] have been demonstrated to transfer mRNAs produced by exogenous DNA plasmids to heterologous cells, but loading and delivery of exogenous DNA, siRNAs and other modified oligonucleotides has not been demonstrated as yet.

SUMMARY OF THE INVENTION

The present inventors have successfully loaded exosomes with exogenous genetic material, and in particular exogenous plasmid DNA, siRNA and modified oligonucleotides. Thus the present invention relates to methods for loading exosomes with exogenous genetic material, the exosomes loaded with such exogenous genetic material, and their use in delivery of the nucleic acid for gene therapy and gene silencing.

The present inventors have also successfully introduced targeting moieties into exosomes so that the exosomes can be targeted to a selected tissue. Thus the present invention relates to exosomes which have a targeting moiety expressed on their surface and to fusion proteins comprising exosomal transmembrane proteins and a targeting moiety, and to nucleic acid constructs encoding such fusion proteins. The exosomes can be loaded with exogenous genetic material, and used in delivery of the nucleic acid for gene therapy and gene silencing.

In accordance with one aspect of the present invention, there is provided a composition comprising an exosome, wherein the exosome is loaded with exogenous genetic material.

In another aspect, the invention provides a composition comprising an exosome containing genetic material, wherein the exosome is derived from an immature dendritic cell, for use in a method of delivering the genetic material in vivo.

In another embodiment, the invention provides a method of loading exosomes with genetic material comprising providing a composition of exosomes, and loading the exosomes with genetic material by electroporation.

In another embodiment, the invention provides a method of loading exosomes with genetic material comprising providing a composition of exosomes and loading the exosomes with nucleic acid by transfection, using a cationic liposome transfection agent.

In accordance with another aspect of the present invention, there is provided a composition comprising an exosome, wherein said exosome comprises a targeting moiety expressed on the surface of the exosome.

In another aspect, the invention provides a polypeptide comprising an exosomal transmembrane protein, and a heterologous targeting peptide, wherein the targeting peptide binds to a moiety present on the surface of the cell to be targeted, and wherein when the polypeptide is present in an exosome, the targeting peptide is present on the surface of the exosome.

In another embodiment, the invention provides a polynucleotide construct encoding a polypeptide, wherein the construct comprises polynucleotide encoding a 5' exosomal transmembrane signal sequence, for example an endoplasmic reticulum-targeting signal peptide operatively linked to polynucleotide encoding the polypeptide of the invention.

In another embodiment, the invention provides a method of targeting an exosome to a selected tissue or cell type comprising transfecting a host cell with a polynucleotide construct according to the invention, expressing the construct in the host cell, and obtaining exosomes from the host cell in which the construct has been expressed.

BRIEF DESCRIPTION OF THE DRAWINGS

FIG. 1A: Electron micrographs of exosomes stained with 2% uranyl acetate (exosomes negatively stained); FIG. 1B: Western blot of exosomes probed with anti-Lamp2, a membrane protein present in exosomes; FIG. 1C: Dynamic light scattering size measurements of purified dendritic cell exosomes in PBS from 5 different purifications FIGS. 2A-2E. Transfection of dendritic cells: FIG. 2A: Modification of Lamp-2b for transfection into dendritic cells. (SP=Signal Peptide; TP=targeting peptide; TM=transmembrane; CT=cytoplasmic tail); FIG. 2B: Western blot with anti-FLAG or anti-Lamp2 in untransfected dendritic cells (CTRL) or cell transfected with pLamp2b-FLAG (FLAG-Lamp2b) and the exosomes harvested from these cells; FIG. 2C: qRT-PCR of dendritic cells transfected with pLamp2b-MSP, -RVG or nothing using primers specific for MSP and RVG sequences.

FIGS. 3A-3D. Electroporation of plasmid with exosome followed by DNase protection assay: FIG. 3A: DNase protection assay on various treatments of exosomes and the pEGFP-NAD plasmid. Linear DNA was made by cutting pEGFP-NAD with EcoRI. (Pre=exosomes pre-electroporated before addition of plasmid); FIG. 3B: Comparison of DNase degradation by DNase with circular plasmid at different electroporation settings; FIG. 3C: DNase protection assay after transfection of pEGFP-NAD with different transfection reagents; FIG. 3D: DNase protection assay after transfection of exosomes with transfection reagents 1-3 and pEGFP-NAD (see materials and methods).

FIG. 4A: Transfection of Neuro2A cells with wild-type exosomes and exosomes expressing RVG-Lamp2b (RVG-exosomes) transfected with pEGFP-NAD compared to plasmid alone after DNase treatment. FIGS. 4B and 4C: qRT-PCR quantification of fold change of eGFP after transfection with normal, RVG- or MSP-exosomes over transfection reagent alone.

FIGS. 5A-5D. Knockdown of GAPDH with exosome-mediated siRNA delivery: FIGS. 5A and 5B: Representative images of Cy5-labelled GAPDH siRNA applied on to Neuro2A (FIG. 5A) and C2C12 (FIG. 5B) cells with normal or modified exosomes. Unelectroporated exosomes and siRNA were added as controls. FIGS. 5C and 5D: qPCR of GAPDH levels in Neuro2A cells and C2C12 cells harvested 2 days after transfection with siRNA alone (siRNA), siRNA with lipofectamine 2000 (Invitrogen) (siRNA+LP), normal exosomes (Exosomes), MSP exosomes (MSP exos) and RVG exosomes (RVG exos). (*p<0.05) Representative Western blots of GAPDH levels after similar transfections were performed (data not shown).

FIGS. 6A and 6B: qPCR of cyclophilin B levels in Neuro2A cells and C2C12 cells harvested 2 days after transfection with siRNA alone (siRNA), siRNA with lipofectamine 2000 (Invitrogen) (siRNA+LP), normal exosomes (Exosomes), MSP exosomes (MSP exos) and RVG exosomes (RVG exos). (*p<0.05) Representative Western blots of cyclophilin B levels after similar transfections were performed (data not shown).

FIG. 7A: Fluorescence correlates linearly to siRNA mass. FIGS. 7B and 7C: Absolute mass of labeled siRNA retained after FIG. 7B, 3 μg of siRNA was electroporated with 3 μg p.e. of RVG-exosomes in 200 μl of buffer at the settings shown on the x-axis; FIG. 7C: 3 μg of siRNA was electroporated with 3 μg p.e. of RVG-exosomes at 400V 125 μF in the volume of buffer shown on the x-axis. All experiments were performed in duplicate.

FIGS. 9A-9D: GAPDH qPCR in the striatum, midbrain, cortex, quadriceps muscle, spleen, liver, kidney and heart of mice 3 days after intravenous injection of 150 μg naked GAPDH siRNA or siRNA encapsulated in unmodified exosomes, MSP-exosomes or RVG-exosomes normalised to untreated controls (100%). FIG. 9E: GAPDH qPCR of RNA extracted from the striatum, cortex and midbrain of untreated mice (control) or mice injected with empty RVG-exosomes intravenously twice on Day 1 and Day 8 then with RVG-exosome-encapsulated GAPDH siRNA (150 μg) on Day 22 before sacrificing the mice on Day 25 (3 injections). FIGS. 9F and 9G: GAPDH qPCR and representative Western blot of mice injected with RVG-exosome encapsulated siRNA (150 μg) on 2 separate occasions 6 and 3 days before sacrifice. Mice were injected intravenously with 150 μg each of two BACE-1 siRNAs encapsulated in 150 μg of RVG-exosomes 3 days before sacrifice and cortical sections were assayed with BACE-1 qPCR (FIG. 9I), BACE-1 Western blot (FIG. 9H) and, β-amyloid 1-42 ELISA (FIG. 9J). All qPCR was normalised to 18S RNA levels. * indicates p<0.05 vs. untreated control. 3 mice were injected in each sample group and all error bars reflect standard deviation (n=3).

DETAILED DESCRIPTION OF THE INVENTION

Figure 1B:
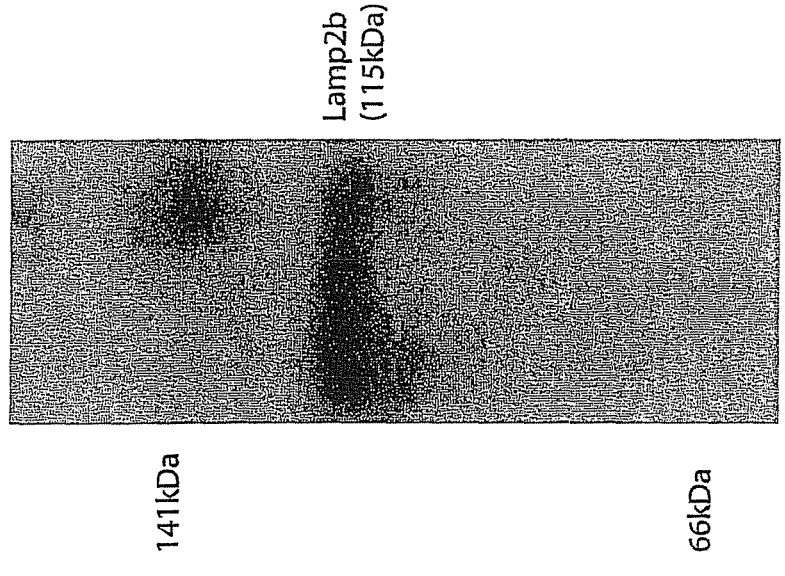
FIGS. 1A-1C. Characterization of exosomes from immature dendritic cells.

The present invention is directed to exosomes, and their use as gene delivery vehicles. Exosomes are small membrane-bound vesicles of endocytic origin that are released into the extracellular environment following fusion of multivesicular bodies with the plasma membrane. Thus, the present application is directed to a composition comprising such exosomes. Typically, the exosomes are between 30 and 100 nm in diameter but can include membrane particles of similar origin up to 200 nm. Exosomes as used herein refers to nanoparticles of endosomal origin that are secreted from multivesicular bodies.

Exosomes are produced by many different types of cells including immune cells such as B lymphocytes, T lymphocytes, dendritic cells (DCs) and most cells. Exosomes are also produced, for example, by glioma cells, platelets, reticulocytes, neurons, intestinal epithelial cells and tumour cells. Exosomes for use in accordance with the present application can be derived from any suitable cell, including the cells identified above. Exosomes have also been isolated from physiological fluids, such as plasma, urine, amniotic fluid and malignant effusions.

In a preferred aspect of the present invention, exosomes are derived from DCs, preferably immature DCs. Exosomes produced from immature DCs do not express MHC-II, MHC-I or CD86. As such, such exosomes do not stimulate naïve T cells to a significant extent and are unable to induce a response in a mixed lymphocyte reaction. Thus exosomes produced from immature dendritic cells are ideal candidates for use in delivery of genetic material, particularly for in vivo use, for example, in gene therapy.

Thus, in accordance with the first aspect of the present invention, exosomes derived from dendritic cells are provided for use in in vivo delivery of genetic material.

In an alternative aspect of the present invention, exosomes can be obtained from any autologous patient-derived, heterologous haplotype-matched or heterologous stem cells so to reduce or avoid the generation of an immune response in a patient to whom the exosomes are delivered. Any exosome-producing cell can be utilized for this specific purpose.

As outlined above, exosomes are produced by many different types of cell and have also been isolated from physiological fluids. Thus, in accordance with the present invention, exosomes can be obtained from any suitable cell type as discussed above, or by isolation from physiological fluids. Typically, the methods of the present invention comprise isolation of the exosomes from cell culture medium or tissue supernatant.

Exosomes produced from cells can be collected from the culture medium by any suitable method. Typically a preparation of exosomes can be prepared from cell culture or tissue supernatant by centrifugation, filtration or combinations of these methods. For example, exosomes can be prepared by differential centrifugation, that is low speed (<20000 g) centrifugation to pellet larger particles followed by high speed (>100000 g) centrifugation to pellet exosomes, size filtration with appropriate filters (for example, 0.22 μm filter), gradient ultracentrifugation (for example, with sucrose gradient) or a combination of these methods.

In accordance with the present invention, the exosomes are loaded with exogenous genetic material. In particular, in accordance with the present invention, exosomes are prepared and then loaded with the desired genetic material for delivery.

Suitable genetic material for delivery includes exogenous DNA plasmid and siRNA. Suitable genetic material also includes modified oligonucleotides and other RNA interference effector moieties such as miRNA and shRNA. In accordance with one aspect of the present invention, the genetic material loaded into the exosome is not genetic material that is typically associated with the exosomes, for example, the nucleic acid is preferably not an mRNA or a miRNA which is incorporated into an exosome on its production from a cell. In particular, the present invention is concerned with the ability to load genetic material into an exosome preparation that has already been isolated from cells. Thus exogenous genetic material refers to genetic material inclusive of nucleic acids that is not normally associated with exosomes. In particularly preferred embodiments, the nucleic acid material is plasmid DNA or other nucleic acids such as siRNA and modified oligonucleotides which are not typically found in exosomes.

Nucleic acids for incorporation into the exosomes may be single or double stranded. Single-stranded nucleic acids include those with phosphodiester, 2'O-methyl, 2' methoxyethyl, phosphoramidate, methylphosphonate, and/or phosphorothioate backbone chemistry. Typically double-stranded nucleic acids are introduced including for example plasmid DNA and small interfering RNAs (siRNAs).

The genetic material to be loaded into the exosomes is chosen on the basis of the desired effect of that genetic material on the cell into which it is intended to be delivered and the mechanism by which that effect is to be carried out. For example, the nucleic acid may be useful in gene therapy, for example in order to express a desired gene in a cell or group of cells. Such nucleic acid is typically in the form of plasmid DNA or viral vector encoding the desired gene and operatively linked to appropriate regulatory sequences such as promoters, enhancers and the like such that the plasmid DNA is expressed once it has been delivered to the cells to be treated. Examples of diseases susceptible to gene therapy include haemophilia B (Factor IX), cystic fibrosis (CTFR) and spinal muscular atrophy (SMN-1).

Nucleic acid can also be used for example in immunisation to express one or more antigens against which it is desired to produce an immune response. Thus, the nucleic acid to be loaded into the exosome can encode one or more antigens against which is desired to produce an immune response, including but not limited to tumour antigens, antigens from pathogens such as viral, bacterial or fungal pathogens.

Nucleic acid can also be used in gene silencing. Such gene silencing may be useful in therapy to switch off aberrant gene expression or in animal model studies to create single or more genetic knock outs. Typically such nucleic acid is provided in the form of siRNAs. For example, RNAi molecules including siRNAs can be used to knock down DMPK with multiple CUG repeats in muscle cells for treatment of myotonic dystrophy. In other examples, plasmids expressing shRNA that reduces the mutant Huntington gene (htt) responsible for Huntington's disease can be delivered with neuron specific exosomes. Other target genes include BACE-1 for the treatment of Alzheimer's disease. Some cancer genes may also be targeted with siRNA or shRNAs, such as ras, c-myc and VEGFR-2. Brain targeted siRNA loaded exosomes may be particularly useful in the silencing of BACE-1 in Alzheimer's disease, silencing of alpha-synuclein in Parkinson's disease, silencing of htt in Huntingdon's disease and silencing of neuronal caspase-3 used in the treatment of stroke to reduce ischaemic damage.

Antisense modified oligonucleotides including 2'-O-Me compounds and PNA can be used. For example, such oligonucleotides can be designed to induce exon-skipping for example the mutant dystrophin gene can be delivered to muscle cells for the treatment of Duchenne Muscular Dystrophy, antisense oligonucleotides which inhibit hairpin loops, for example in the treatment of myotonic dystrophy and trans-splicing oligonucleotides, for example for the treatment of spinal muscular atrophy.

The exogenous genetic material can be introduced into the exosomes by a number of different techniques. In particularly preferred embodiments of the invention, the exosomes are loaded by electroporation or the use of a transfection reagent. The present inventors have identified that despite the small size of exosomes, it is still possible to use electroporation to load the exosomes with the exogenous genetic material. This is surprising in view of the small size of the exosomes compared to cells. Extrapolation of the voltages used for electroporation of cells to take into account the size of the exosomes would suggest that excessively high voltages would be required for electroporation of exosomes. Surprisingly however, the present inventors have identified that it is possible to use electroporation to load exosomes with plasmid DNA and siRNA. Typical voltages are in the range of 20V/cm to 1000V/cm, such as 20V/cm to 100V/cm with capacitance typically between 25 µF and 250 µF, such as between 25 µF and 125 µF.

In an alternative aspect of the present invention, the inventors have also identified that it is possible to load exosomes using transfection agents. Despite the small size of the exosomes, conventional transfection agents can be used for transfection of exosomes with genetic material. Preferred transfection reagents for use in accordance with the present invention include cationic liposomes.

Targeting

The present invention also relates to the targeting of exosomes to a desired cell type or tissue. This targeting is achieved by expressing on the surface of the exosome a targeting moiety which binds to a cell surface moiety expressed on the surface of the cell to be targeted. Typically the targeting moiety is a peptide which is expressed as a fusion protein with a transmembrane protein typically expressed on the surface of the exosome.

In more detail, the exosomes can be targeted to particular cell types or tissues by expressing on their surface a targeting moiety such as a peptide. Suitable peptides are those which bind to cell surface moieties such as receptors or their ligands found on the cell surface of the cell to be targeted. Examples of suitable targeting moieties are short peptides, scFv and complete proteins, so long as the targeting moiety can be expressed on the surface of the exosome and does not interfere with insertion of the membrane protein into the exosome. Typically the targeting peptide is heterologous to the transmembrane exosomal protein. Peptide targeting moieties may typically be less than 100 amino acids in length, for example less than 50 amino acids in length, less than 30 amino acids in length, to a minimum length of 10, 5 or 3 amino acids.

Targeting moieties can be selected to target particular tissue types such as muscle, brain, liver, pancreas and lung for example, or to target a diseased tissue such as a tumour.

In a particularly preferred embodiment of the present invention, the exosomes are targeted to brain tissue.

Specific examples of targeting moieties include muscle specific peptide, discovered by phage display, [33] to target skeletal muscle, a 29 amino acid fragment of Rabies virus glycoprotein that binds to the acetylcholine receptor [36] or a fragment of neural growth factor that targets its receptor [37] to target neurons and secretin peptide that binds to the secretin receptor can be used to target biliary and pancreatic epithelia [38]. As an alternative, immunoglobulins and their derivatives, including scFv antibody fragments can also be expressed as a fusion protein to target specific antigens, such as VEGFR for cancer gene therapy. As an alternative, natural ligands for receptors can be expressed as fusion proteins to confer specificity, such as NGF which binds NGFR and confers neuron-specific targeting.

The peptide targeting moiety is expressed on the surface of the exosome by expressing it as a fusion protein with an exosomal transmembrane protein. A number of proteins are known to be associated with exosomes; that is they are incorporated into the exosome as it is formed. The preferred proteins for use in accordance with the present invention are those which are transmembrane proteins. Examples include but are not limited to Lamp-1, Lamp-2, CD13, CD86, Flotillin, Syntaxin-3, CD2, CD36, CD40, CD40L, CD41a, CD44, CD45, ICAM-1, Integrin alpha4, L1CAM, LFA-1, Mac-1 alpha and beta, Vti-1A and B, CD3 epsilon and zeta, CD9, CD18, CD37, CD53, CD63, CD81, CD82, CXCR4, FcR, GluR2/3, HLA-DM (MHC II), immunoglobulins, MHC-I or MHC-II components, TCR beta and tetraspanins. In particularly preferred embodiments of the present invention, the transmembrane protein is selected from Lamp-1, Lamp-2, CD13, CD86, Flotillin, Syntaxin-3. In a particularly preferred embodiment the transmembrane protein is Lamp-2. The sequence of Lamp-2 is set out in SEQ ID No 1.

The following section relates to general features of all polypeptides of the invention, and in particular to variations, alterations, modifications or derivatisations of amino acid sequence which are included within the polypeptides of the invention. It will be understood that such variations, alterations, modifications or derivatisations of polypeptides as are described herein are subject to the requirement that the polypeptides retain any further required activity or characteristic as may be specified subsequent sections of this disclosure.

Variants of polypeptides of the invention may be defined by particular levels of amino acid identity which are described in more detail in subsequent sections of this disclosure. Amino acid identity may be calculated using any suitable algorithm. For example the PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (www.ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate homology (for example used on its default settings) (Devereux et al (1984) *Nucleic Acids Research* 12, 387-395).

It will be understood that variants of polypeptides of the invention also includes substitution variants. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

The amino acid sequence of polypeptides for use in the invention may be modified to include non-naturally occurring chemistries or to increase the stability and targeting specificity of the compound. When the polypeptides are produced by synthetic means, such amino acids may be introduced during production. The polypeptides may also be modified following either synthetic or recombinant production.

A number of side chain modifications are known in the art and may be made to the side chains of the polypeptides, subject to the polypeptides retaining any further required activity or characteristic as may be specified herein.

Variant polypeptides as described in this section are those for which the amino acid sequence varies from that in SEQ ID NO: 1, but which retain the ability to be inserted into the membrane of an exosome.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made, provided the modified polypeptide is inserted into the membrane of an exosome.

Typically, polypeptides which are variants of Lamp-2 have more than about 50%, 55% or 65% identity, preferably at least 70%, at least 80%, at least 90% and particularly preferably at least 95%, at least 97% or at least 99% identity, with the amino acid sequence of SEQ ID NO: 1. The identity of variants of SEQ ID NO: 1 may be measured over a region of at least 30, 50, 100, 200, 250, 300, 350 or more contiguous amino acids of the sequence shown in SEQ ID NO: 1, or more preferably over the full length of SEQ ID NO: 1, excluding the signal sequence.

The fragment of the Lamp-2 polypeptide used in the invention is typically at least 55 amino acids, 100, 150, 200, or 250 amino acids in length.

The exosomal transmembrane protein is modified to incorporate a targeting moiety. Thus the exosomal transmembrane protein is expressed as a fusion protein comprising the targeting moiety. The targeting moiety is incorporated into the transmembrane protein such that it is positioned in the portion of the transmembrane protein present on the surface of the exosomes. In a preferred aspect of the present invention, the exosomal transmembrane protein is Lamp-2 and the targeting moiety is expressed as a fusion protein, wherein the targeting moiety is present near the N-terminus of Lamp-2 protein for example within 30, or within 20 amino acids of the Lamp-2 N terminal amino acid, not including the signal sequence.

Spacer or linker sequences may be provided between the targeting moiety and the remainder of the transmembrane protein for example to avoid interference from the targeting moiety in the folding of the transmembrane protein.

Linker or spacer sequences are typically 1 to 10 amino acids in length, typically 1 to 8 amino acids in length such as 2, 3 or 4 amino acids in length. Suitable amino acids for incorporation in linkers are alanine, arginine, serine or glycine. Suitable linkers include Ala-Arg and Ser-Gly-Gly.

In a particularly preferred aspect of the present invention, the transmembrane protein is Lamp-2 and the targeting moiety is present at or near the N-terminus of the protein, separated from Lamp-2 with linker sequences.

In the practice of the present invention, the targeting moiety is introduced into the exosome by expressing the fusion protein comprising the targeting moiety and exosomal transmembrane protein within a cell used to produce the exosomes. Expression of this fusion protein in the cell, allows for the fusion protein to be incorporated into the exosome as it is produced from the cell.

For example, a polynucleotide construct such as a DNA plasmid, which expressed the fusion protein is transfected into the cell. Any suitable method can be used for introduction of the polynucleotide construct into the cell. The polynucleotide construct includes suitable promoter sequences so that the encoded fusion protein is expressed in the cell. Signal peptide sequences are also included so that the protein is incorporated into the membrane of the endoplasmic reticulum as it is produced. The membrane protein is then subsequently exported to the exosomal/lysomal compartment before incorporation into the exosome. The signal sequence is typically a signal peptide sequence for an exosomal transmembrane protein. For example the signal peptide sequence is preferably derived from Lamp-2, for example as shown in the Examples.

Preferred cells for production of exosomes are discussed in more detail above. Typically a preferred cell, such as an immature dendritic cells is transfected with a polynucleotide construct as described above, such that the fusion protein of the invention is expressed in the cell. Exosomes produced by the cell can then be collected. Such exosomes have the fusion protein inserted into the membrane such that the exosomes are targeted to the desired tissue or cell type through the targeting moiety.

Exosomes produced from cells can be collected from the culture medium by any suitable method. Typically a preparation of exosomes can be prepared from cell culture or tissue supernatant by centrifugation, filtration or combinations of these methods. For example, exosomes can be prepared by differential centrifugation, that is low speed (<20000 g) centrifugation to pellet larger particles followed by high speed (>100000 g) centrifugation to pellet exosomes, size filtration with appropriate filters (for example, 0.22 µm filter), gradient ultracentrifugation (for example, with sucrose gradient) or a combination of these methods.

In accordance with a preferred aspect of the present invention, the targeted exosomes are loaded with exogenous genetic material. In particular, in accordance with the present invention, exosomes are prepared with a targeting moiety as described herein and then loaded with the desired genetic material for delivery or described above.

In other embodiments of the invention, a specific targeting moiety does not need to be included in the exosome. For example, exosomes may be administered directly to the site where therapy is required. Alternatively, for example, where exosomes contain genetic material encoding immunogens, direct targeting to a specific site may not be required and delivery, for example, intradermal or muscular delivery may be sufficient to generate the desired immune response without targeting exosomes to any specific cell type.

In some embodiments of the invention, no targeting moiety is included on the surface of the exosomes. However, the exosomes are selected such that they are more likely to target a specific tissue type. For example, exosomes derived from different cells may have natural affinities for specific cell subtypes as required by their physiological function such as the well-established affinity of mature dendritic cell-derived exosomes to T-cells. This affinity may be utilized to specifically deliver above-mentioned cargo to a tissue.

Delivery/Administration

The constructs of the invention may be administered by any suitable means. Administration to a human or animal subject may be selected from parenteral, intramuscular, intracerebral, intravascular, subcutaneous, or transdermal administration. Typically the method of delivery is by injection. Preferably the injection is intramuscular or intravascular (e.g. intravenous). A physician will be able to determine the required route of administration for each particular patient.

The constructs are preferably delivered as a composition. The composition may be formulated for parenteral, intramuscular, intracerebral, intravascular (including intravenous), subcutaneous, or transdermal administration. Compositions for parenteral administration may include sterile aqueous solutions which may also contain buffers, diluents and other suitable additives. The constructs of the invention may be formulated in a pharmaceutical composition, which may include pharmaceutically acceptable carriers, thickeners, diluents, buffers, preservatives, and other pharmaceutically acceptable carriers or excipients and the like in addition to the exosomes.

A "pharmaceutically acceptable carrier" (excipient) is a pharmaceutically acceptable solvent, suspending agent or any other pharmacologically inert vehicle for delivering one or more nucleic acids to a subject. Typical pharmaceutically acceptable carriers include, but are not limited to, binding agents (e.g. pregelatinised maize starch, polyvinylpyrrolidone or hydroxypropyl methylcellulose, etc); fillers (e.g. lactose and other sugars, microcrystalline cellulose, pectin, gelatin, calcium sulfate, ethyl cellulose, polyacrylates or calcium hydrogen phosphate, etc); lubricants (e.g. magnesium stearate, talc, silica, colloidal silicon dioxide, stearic acid, metallic stearates, hydrogenated vegetable oils, corn starch, polyethylene glycols, sodium benzoate, sodium acetate, etc); disintegrates (e.g. starch, sodium starch glycolate, etc); or wetting agents (e.g. sodium lauryl sulphate, etc).

The compositions provided herein may additionally contain other adjunct components conventionally found in pharmaceutical compositions. Thus, for example, the compositions may contain additional compatible pharmaceutically-active materials or may contain additional materials useful in physically formulating various dosage forms of the composition of present invention, such as dyes, flavouring agents, preservatives, antioxidants, opacifiers, thickening agents and stabilizers. However, such materials, when added, should not unduly interfere with the biological activities of the components of the compositions provided herein.

A therapeutically effective amount of composition is administered. The dose may be determined according to various parameters, especially according to the severity of the condition, age, and weight of the patient to be treated; the route of administration; and the required regimen. A physician will be able to determine the required route of administration and dosage for any particular patient. Optimum dosages may vary depending on the relative potency of individual constructs, and can generally be estimated based on EC50s found to be effective in vitro and in in vivo animal models. In general, dosage is from 0.01 mg/kg to 100 mg per kg of body weight. A typical daily dose is from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. Different dosages of the construct may be administered depending on whether administration is by intramuscular injection or systemic (intravenous or subcutaneous) injection. Preferably, the dose of a single intramuscular injection is in the range of about 5 to 20 µg. Preferably, the dose of single or multiple systemic injections is in the range of 10 to 100 mg/kg of body weight.

Due to construct clearance (and breakdown of any targeted molecule), the patient may have to be treated repeatedly, for example once or more daily, weekly, monthly or yearly. Persons of ordinary skill in the art can easily estimate repetition rates for dosing based on measured residence times and concentrations of the construct in bodily fluids or tissues. Following successful treatment, it may be desirable to have the patient undergo maintenance therapy, wherein the construct is administered in maintenance doses, ranging from 0.01 mg/kg to 100 mg per kg of body weight, once or more daily, to once every 20 years.

The invention is hereinafter described in more detail with reference to the following Examples.

Examples

We aimed to determine if exosomes can be reproducibly produced from dendritic cells harvested from murine bone marrow. Using a protocol modified from Quah et al. [28], bone marrow cells were harvested from femurs of C57BL/6 mice, dissociated with gentle mashing and cultured in the presence of DC medium (refer materials and methods) with 10 ng/ml GM-CSF, which stimulates proliferation of progenitor cells. Non-adherent cells were removed after 4 days, leaving dendritic cells in culture. After 7 days, GM-CSF is removed and fresh DC medium without GM-CSF is added to isolate exosomes. Exosomes are harvested daily over the next 2 days by centrifugation of culture supernatant, first at 10,000 g to remove cellular debris, then at 120,000 g to pellet exosomes. The exosomes are then resuspended in an appropriate amount of 0.1M ammonium acetate buffer.

Figure 1A:
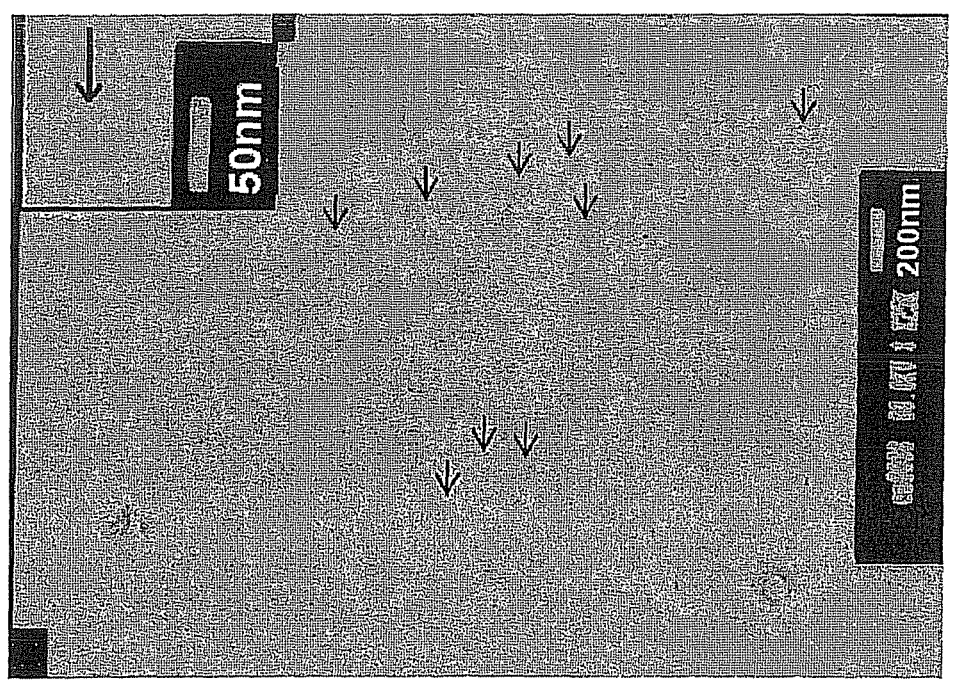
Figure 1C:
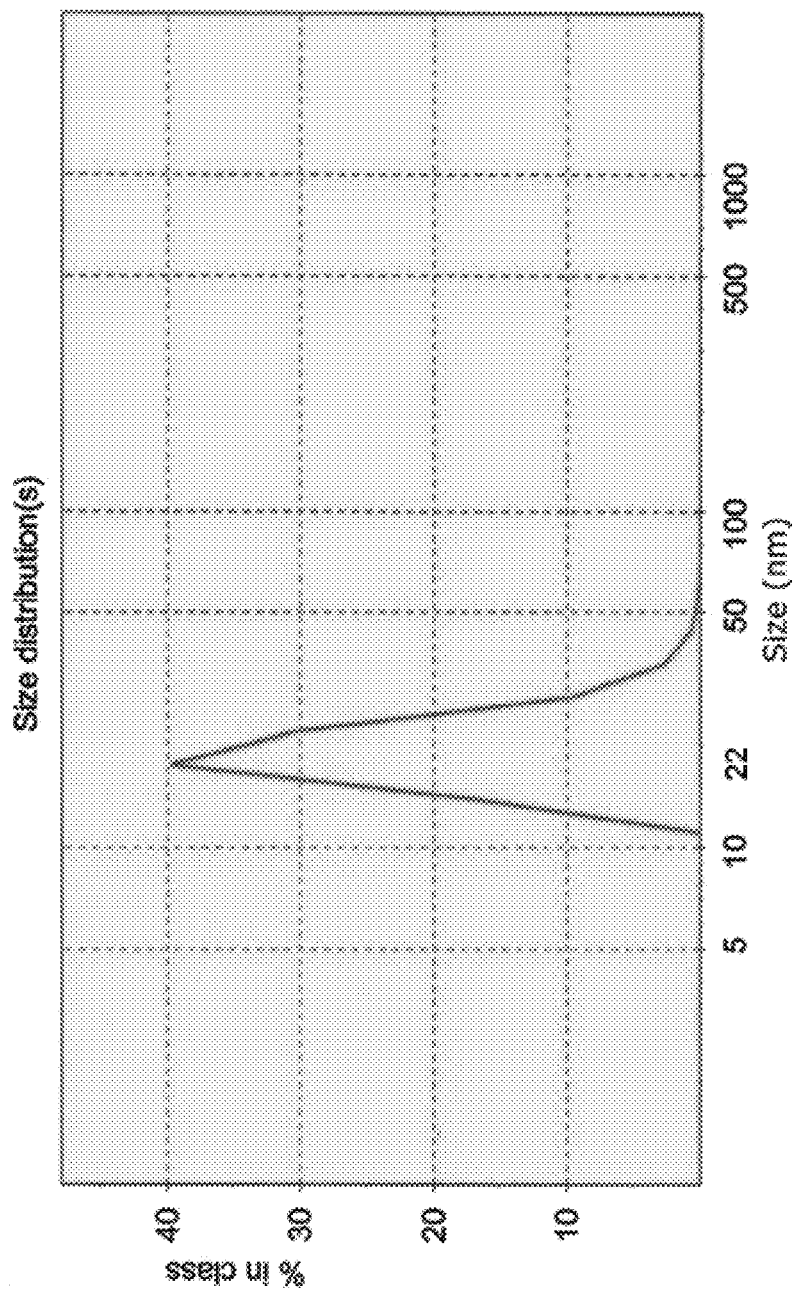
Figure 1C:
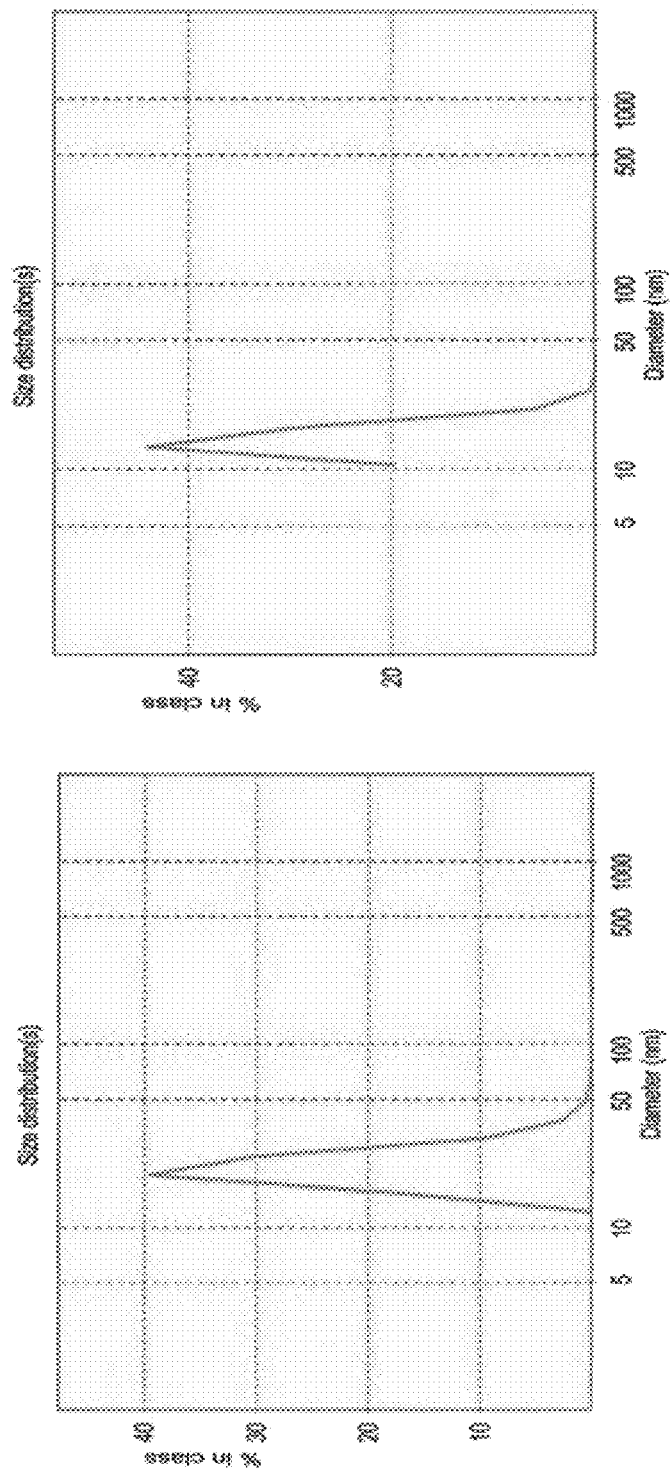

The exosomes produced were consistent and physically homogenous, with a size distribution peaking at 80 nm in diameter as determined by electron microscopy (FIG. 1A), Western with an antibody against an exosomal protein (Lamp2b) (FIG. 1B) and dynamic light scattering (FIG. 1C).

Transfection of a targeting ligand is required to alter the specificity of the exosomes in order to effectively target desired cell types. FIG. 2A illustrates how a targeting ligand is inserted into Lamp2b. As it is a type I membrane protein with an N-terminus predicted to protrude out of the exosome, the targeting ligand needs to be attached to the N-terminus after the signal peptide. The signal peptide is required for membrane insertion but is cleaved off in the mature protein. In addition, the targeting peptide is flanked by linkers (Ala-Arg-{Targeting Peptide}-Ser-Gly-Gly) to prevent the targeting peptide from influencing the folding of the Lamp2b protein. Ultimately, the targeting peptide should be located on the external surface of the exosomes, hence conferring targeting capabilities to the exosomes. Three different peptides—the neuron-specific rabies viral glycoprotein (RVG) peptide (YTIWMPENPRPGTPCDIFTNSRGKRASNG (SEQ ID No: 6)) [32], a muscle-specific peptide (MSP) identified by in vivo phage display (ASSLNIA) (SEQ ID No: 9) [33], and a FLAG epitope—were separately cloned into Lamp2b and transfected into the dendritic cells 4 days before exosome purification. Both MSP and RVG were selected for organ specificity while the FLAG epitope in the targeting ligand site was used to differentiated modified Lamp2b and unmodified exogenous Lamp2b. A major hindrance to the ability to express targeting ligands on the surface of exosomes is that primary dendritic cells are difficult to transfect and can potentially differentiate after transfection. Infection with viral vectors is not ideal either as dendritic cells are likely to be activated by the virus [30], hence producing immunostimulatory molecules that will be incorporated into the resultant exosomes. Hence, a number of transfection reagents were tested and Minis Bio's TransIT-LT1 reagent was selected as it appeared to efficiently transduce dendritic cells, with a 49900 fold increase in eGFP mRNA normalized to murine GAPDH over the addition by pEGFP-NAD, an eGFP-expressing plasmid, alone without transfection reagents. More importantly, this transfection does not appear to significantly activate dendritic cells based on observation of cell morphology. Immature dendritic cells are compact rounded cells with low surface area-to-volume ratios while activated dendritic cells have characteristic dendritic extensions and large surface area-to-volume ratios [31].

Meanwhile, Western blot against the FLAG ligand clearly demonstrates that FLAG-Lamp2b (115 kDa) is expressed in dendritic cells and corresponding exosomes after transfection of pLamp2b-FLAG but not in normal cells and exosomes (FIG. 2B). Expression of MSP-Lamp2b and RVG-Lamp2b was verified with qRT-PCR of dendritic cells transfected with pLamp2b-MSP and pLamp2b-RVG using specific primers for the MSP and RVG sequences (FIG. 2C).

Figure 2D:
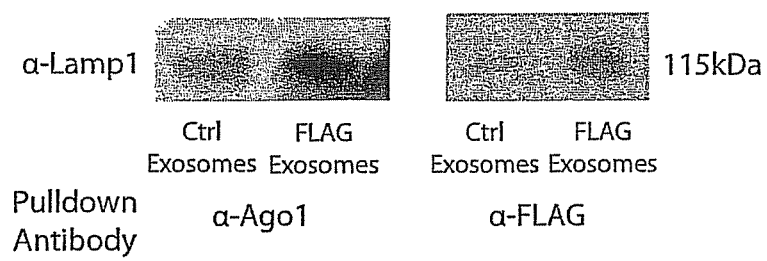
FIG. 2D: Western blot with anti-Lamp1 after incubation of normal exosomes and FLAG exosomes with anti-FLAG beads or anti-AGO1 beads (non-binding control) in an exosome pulldown assay.
Figure 2E:
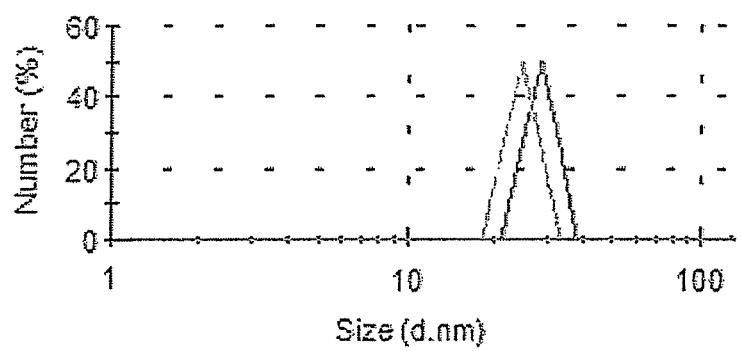
FIG. 2E: Dynamic light scattering size measurements of purified MSP-exosomes.

As the topology of Lamp2b on exosomes was unknown, a pulldown assay with anti-FLAG beads was designed to establish the orientation of the targeting epitope. Anti-FLAG antibody or a non-specific antibody (Ago1) was bound to protein-A Sepharose beads (Sigma). These beads were then incubated with unmodified or FLAG-exosomes before 3 washes to remove non-binders. If the FLAG epitope was exclusively internal and inaccessible to the antibody, neither unmodified nor FLAG-exosomes should be retained on the beads; if the FLAG epitope was external, FLAG-exosomes would be retained but not unmodified exosomes. Following pulldown, the retained exosomes were denatured and detected by Western blot against LAMP-1, another exosomal protein that serves as a marker for the presence of exosomes. Western blot for Lamp1, another exosome-specific protein, showed increased retention of FLAG-exosomes by anti-FLAG beads but not by control anti-Ago-1 (non-specific) beads (FIG. 2D). This result demonstrates that the targeting moiety is localized to the external exosomal surface and validating its targeting potential. These modifications do not appear to affect the physical properties of the modified exosomes based on dynamic light scattering of MSP-exosomes (FIG. 2E).

Protocol: Transfection of Dendritic Cells

Transfection of dendritic cells was performed with 5 µg of pEGFP-NAD or pLamp2b derivatives and 5 µl of TransIT LT1 transfection reagent (Minis Bio) in a 6-well plate with $10^6$ cells on Day 4 after harvesting. Medium is changed on Day 7 and exosomes are isolated from culture supernatant on Day 8.

PROTOCOL: Transfection and Electroporation with Exosomes and DNase Protection Assay For the following experiments, an EGFP-expressing plasmid, pEGFP-NAD, was used as DNA cargo, Cy5-labeled anti-GAPDH siRNA and unlabelled anti-mouse cyclophilin B were used as RNA cargo and a Cy3-labeled 2'-OMe oligonucleotide and a Cy3-labelled morpholino designed for exon skipping in mdx mice (gift from Haifang Yin) were used.

Figure 3A:
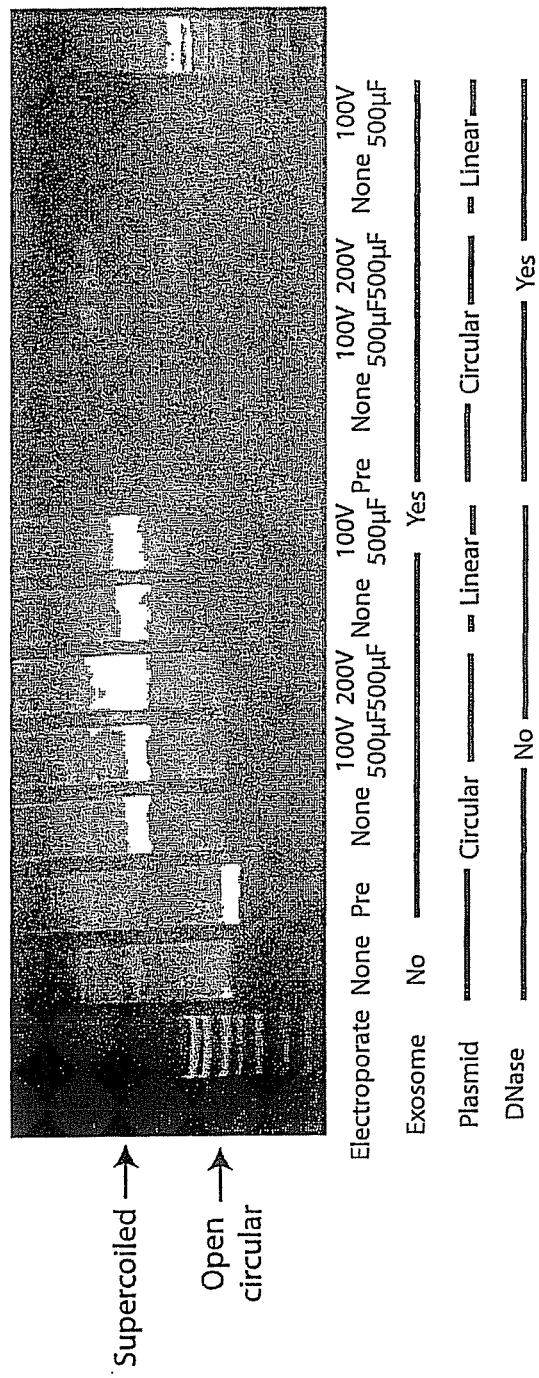

Circular and linearized pEGFP-NAD were electroporated with exosomes and then exposed to DNase I for 10 minutes. If the DNA was successfully loaded in to the exosomes, the DNase will be unable to digest the DNA as it is unable to access the interior of the exosomes; conversely, if the DNA was not located within the exosomes, the presence of DNase will result in DNA degradation and the loss of a plasmid signal. When a DNase protection assay was performed on plasmid DNA, electroporation with exosomes appear to protect circular DNA plasmid from degradation but not linear DNA (FIG. 3A) and that lower capacitance appears to increase uptake of DNA into exosomes (FIG. 3B). To exclude the possibility that factors released from the exosomes by electroporation inhibited DNase activity, DNA was added to pre-electroporated exosomes as a control. In addition to that, it appears the super-coiled fraction is preferentially protected (higher band). This may be because exosomes are themselves 20-30 nm yet an open circular plasmid 1868 nt in length can be over 100 nm in diameter, while a supercoiled plasmid is more compact and takes up significant less volume [34], hence supercoiled plasmids are preferentially protected.

The difficulty of coming up with a suitable electroporation protocol is highlighted by inconsistent results and often low level of protection even when successful (results not shown). Artificially condensing DNA with spermine resulted in reduced DNase protection (results not shown), possibly because the concentration of spermine used is extremely critical in producing condensates of the right size [35]. Too little and no condensation occurs, but too much and large aggregates form, which may be the reason why the addition of spermine actually decreased the levels of DNase protection.

A separate approach utilizing transfection instead of electroporation resulted in significant DNase protection for open circular plasmids. 1 μg of the pEGFP-NAD plasmid was mixed with 1 μl of the transfection reagent, exosomes (3 μg) and topped up to 100 μl with DMEM. The solution was incubated for 3 hours at 37° C. and then subjected to DNase treatment for 10 minutes at 37° C. with the addition of 1 μl of RQ DNase I (Promega) and 10 μl of RQ DNase buffer. The DNase was inactivated by 10 μl of STOP buffer (Promega) before the DNase protection assay or the direct addition of the entire solution to Neuro2A or C2C12 cells in a 24-well format. Three different transfection reagents (1:Lipofectamine 2000 (Invitrogen); 2:TransIT LT1 (Minis Bio) 3: TurboFect (Fermantas)) were used to deliver open circular pEGFP-NAD into exosomes and preliminary results suggest that Reagent 3 resulted in significant DNase protection (FIG. 3D), suggesting that transfection reagents can be used to load genetic cargo into exosomes. The control experiments with transfection reagent alone seem to indicate the transfection reagent does not confer protection by itself (FIG. 3C). Despite the fact that open circular plasmids are predicted to be too large for exosomes, the addition of transfection reagent may serve to condense the plasmids as well as provide additional hydrophobic molecules to increase the size of the exosomes.

For the DNase protection Assay, 20 μl of the electroporated solution was added to 70 μl of distilled water, 10 μl of RQ DNase Buffer and 1 μl RQ DNase I (Promega) and incubated at 37° C. for 10 min before inhibiting the reaction with 10 μl of STOP buffer. 10 μl of each sample was run on each lane in a 0.8% agarose TAE gel.

PROTOCOL: Delivery of Genetic Material by Exosomes into Neuro2A and C2C12 Cells

Figure 4A:
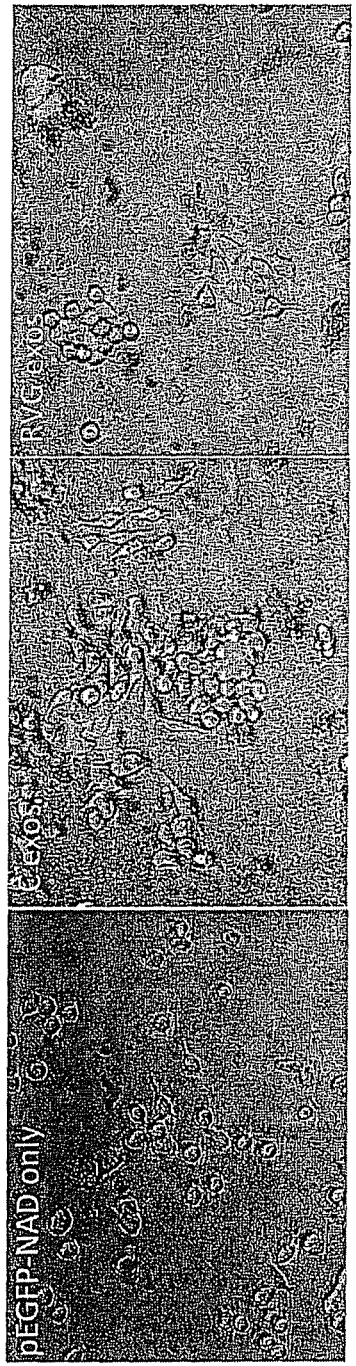
FIGS. 4A-4C. Exosome-mediated delivery of pEGFP-NAD into cells.
Figure 4C:
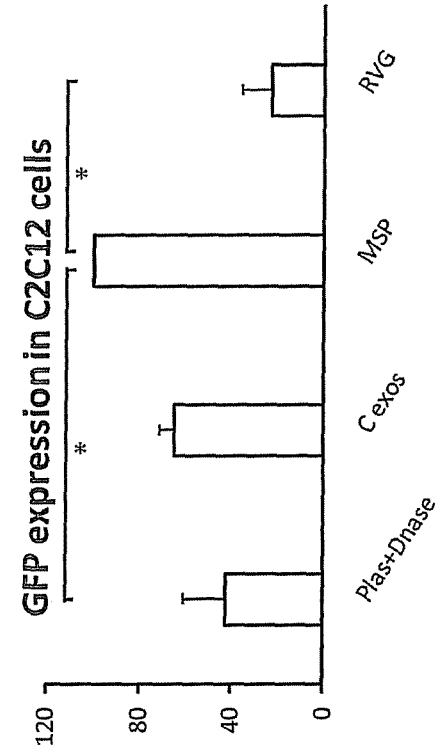
Figure 4B:
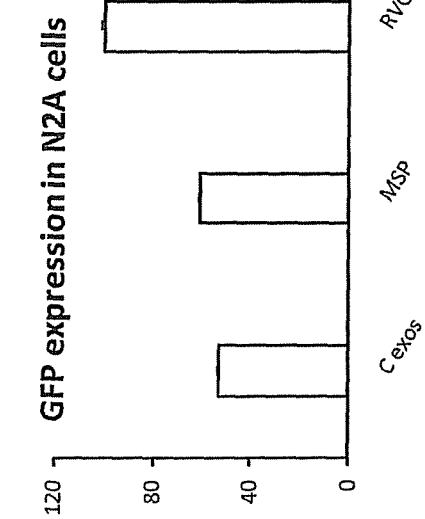

Since exosomes were found to take up DNA plasmids readily upon electroporation and transfection, we hypothesized that exosomes loaded with pEGFP-NAD would be able to transfect cells in vitro. We added transfection reagent 3 (FIG. 3C) to pEGFP-NAD without exosomes, with wild type exosomes, or with exosomes harvested from dendritic cells transfected with pLamp2b-RVG (RVG-exosomes) or pLamp2b-MSP (MSP-exosomes) and DNase treated the mixture after incubation, including the sample with pEGFP-NAD and transfection reagent alone. The cells were then transfected directly with the mixture for 2 days and results suggest that both at the RNA level through qRT-PCR (FIGS. 4B and 4C) and at the protein level through GFP fluorescence (FIG. 4A), exosomes efficiently transferred pEGFP-NAD into target cells. In addition, results suggest that RVG and MSP peptides improve the uptake of pEGFP-NAD by increasing affinity to Neuro2A and C2C12 cells exclusively and this phenomenon is cell type-dependent.

Figure 5C:
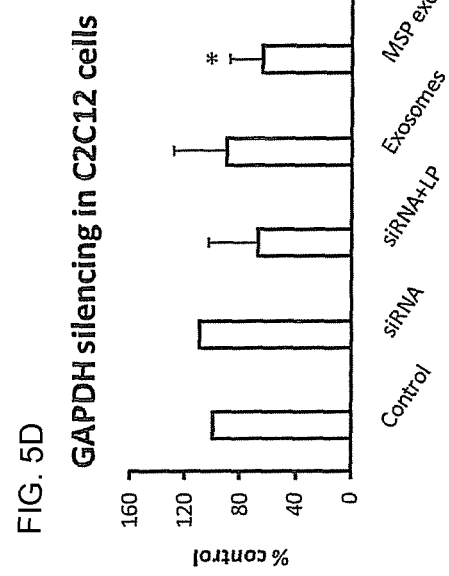
Figure 5D:
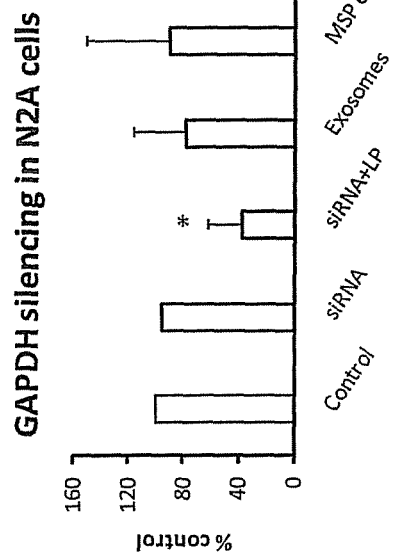

Given that exosomes were able to take up DNA plasmids and contain RNA naturally [26], siRNAs should also be readily taken up by exosomes. We hypothesized that exosomes would also be able to deliver siRNAs. Hence, a well characterized Cy5-labeled siRNA against GAPDH (Ambion) was electroporated into wild type, RVG- and MSP-exosomes and applied directly to Neuro2A and C2C12 cells. The cells were then imaged after 2 days and showed higher fluorescence when compared to control cells treated with siRNA and unelectroporated exosomes alone (FIGS. 5A and 5B). Similar protocols were followed for the transfection of cells with exosomes and qRT-PCR of GAPDH normalised to 18S RNA (FIGS. 5C and 5D) demonstrated significant knockdown in targeted exosomes compared to controls after 2 days, suggesting that the siRNAs were released into the cytoplasm after transfection to actively repress the endogenous target and that the targeting moiety effectively delivered the siRNA to the desired cell type i.e. neuron-specific RVG to neuronal Neuro2A cells and muscle specific MSP to C2C12 myoblasts. This knockdown was further confirmed with Western blot of the GAPDH protein (FIGS. 5E and 5F).

As further evidence of specific delivery, a second siRNA against murine cyclophilin B (PPIB) (Ambion) was also transfected similarly and demonstrated similar patterns of knockdown (FIG. 6) as measured by qPCR and Western blots.

Figure 7A:
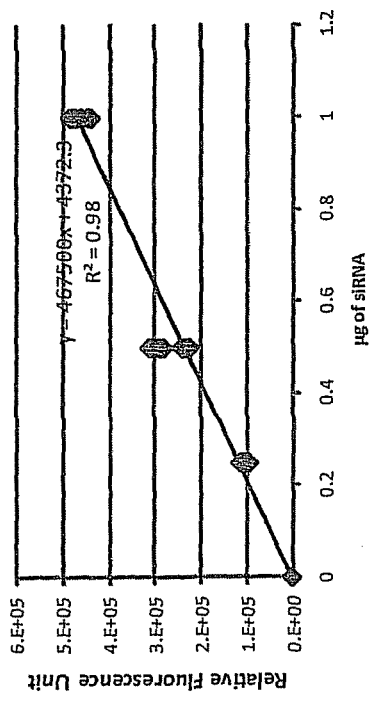
FIGS. 7A-7C. Retention of Cy3 and Cy5 labeled siRNA after electroporation with exosomes.
Figure 7C:
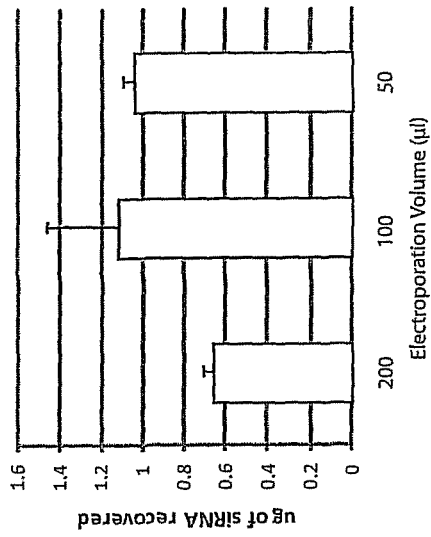
Figure 7B:
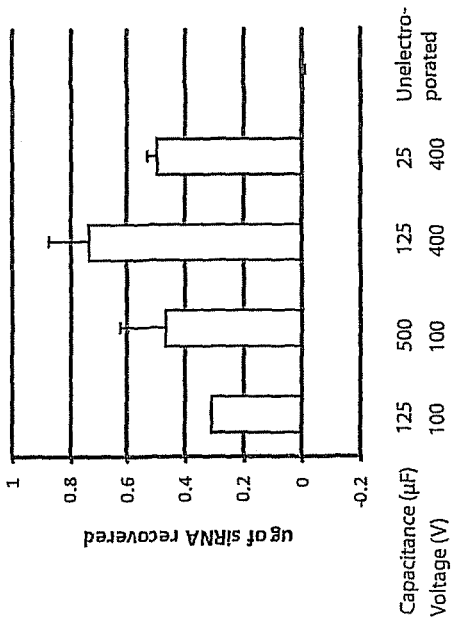

In order to quantify the loading efficiency of different electroporation protocols, 3 μg of murine PPIB siRNA labelled with a Cy3 and a Cy5 fluorophore on either strand was mixed with 3 μg p.e. of RVG-exosomes, added to an electroporation buffer based on Eppendorf Hypoosmolar Buffer and electroporated on a Biorad GenePulsar II in a 4 mm cuvette. The mixture was then diluted with PBS and spun down at 120,000 g for 60 minutes to purify the exosomes. The resultant pellet was resuspended in 100 μl of double distilled water, which is predicted to lyse the exosomes via osmotic pressure and release the encapsulated siRNA within. The siRNA content was then measured with a fluorescence plate reader with 560 nm excitation and 610 nm emission and the retained siRNA quantified against a standard curve of pure siRNA in water. As shown in FIG. 7, over 20% of initial siRNA (0.73 m) was retained after electroporation at 400V and 125 μF, the optimum electroporation setting. Furthermore, concentrating the mixture by decreasing the amount of electroporation buffer appeared to increase the loading up to a certain level.

Figure 8A:
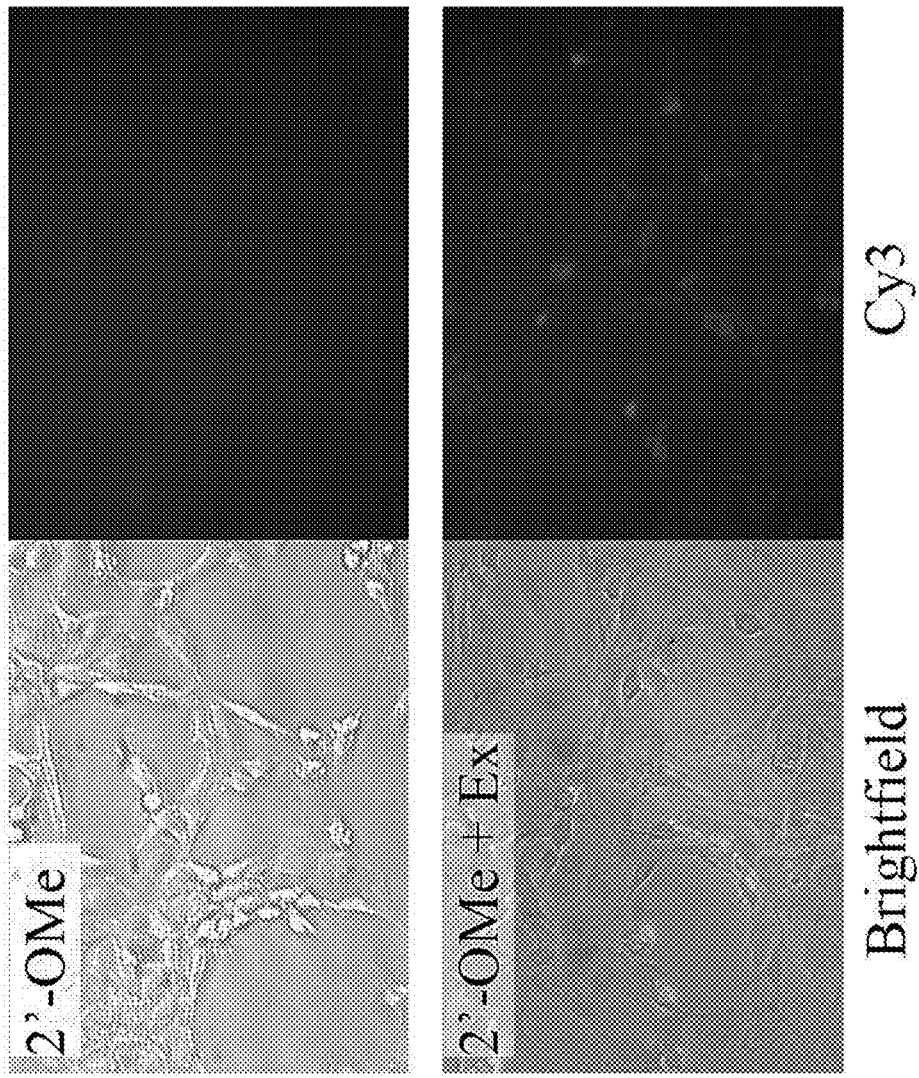
FIGS. 8A and 8B. Delivery of 2'-OMe oligonucleotide and morpholinos with normal exosomes: Fluorescence imaging of C2C12 cells 24 hours after Cy3-labelled (FIG. 8A) 2'-OMe oligonucleotides or (FIG. 8B) PMO transfection with or without exosomes.
Figure 8B:
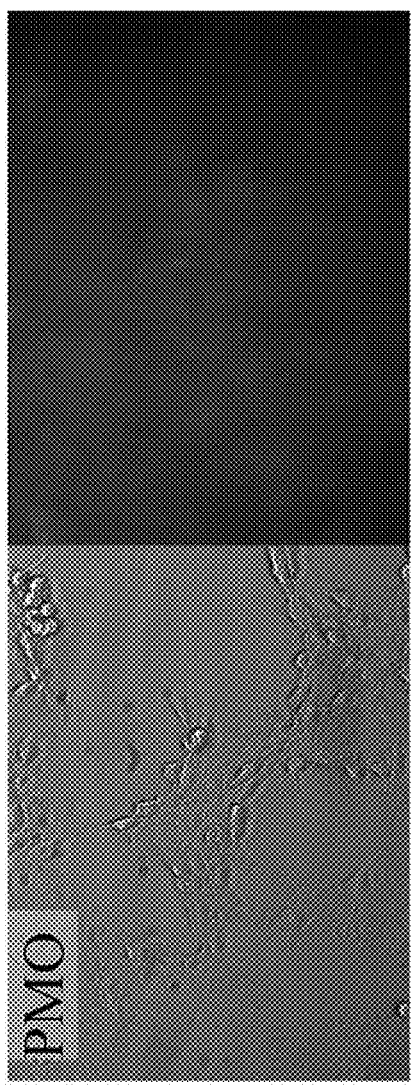
Figure 8B:
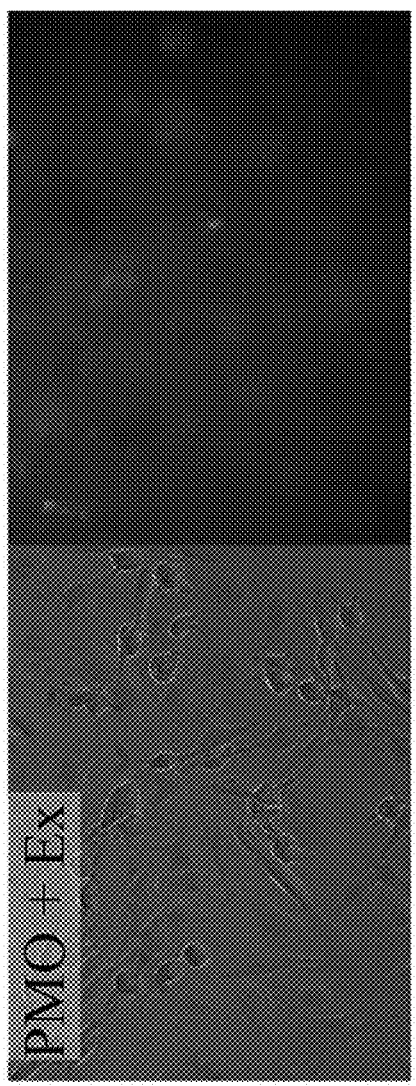

Finally, transfection of labeled 2'-OMe oligonucleotide (100 pmoles) and PMO (100 pmoles) were attempted with normal exosomes in C2C12 cells and imaged a day after application. Of the two types of small oligonucleotide species, 2'-OMe oligonucleotide appears to be effectively delivered into C2C12 cells (FIG. 8A) while morpholino (PMO) delivery does not appear to be improved by exosome-mediated delivery with unmodified exosomes (FIG. 8B). From this experiment, we believe it is possible for us to load a variety of unnatural oligonucleotides into the exosome for delivery, including 2'-OMe, morpholino, thio-nucleotides, chemically modified siRNAs and peptide nucleic acids.

Materials

Unless otherwise stated, all chemicals were obtained from Sigma-Aldrich UK and all enzymes used were obtained from New England Biolabs.

Cell Culture

Dendritic cells were cultured in DC medium (DMEM Glutamax, 10% FBS, non-essential amino acids # and antibiotics). C2C12 cells were cultured in DMEM Glutamax supplemented with 20% FBS and antibiotics. Neuro2A cells were cultured in EMEM supplemented with 10% FBS. All cells were incubated at 37° C. in 5% $CO_2$.

Plasmids

Figure 6A:
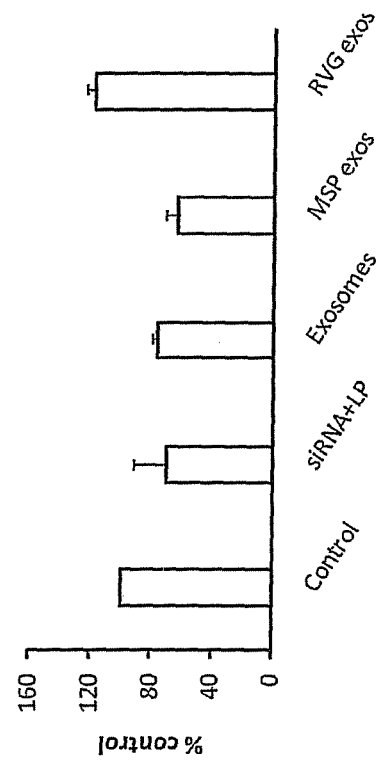
FIGS. 6A-6B. Knockdown of cyclophilin B with exosome-mediated siRNA delivery.
Figure 6B:
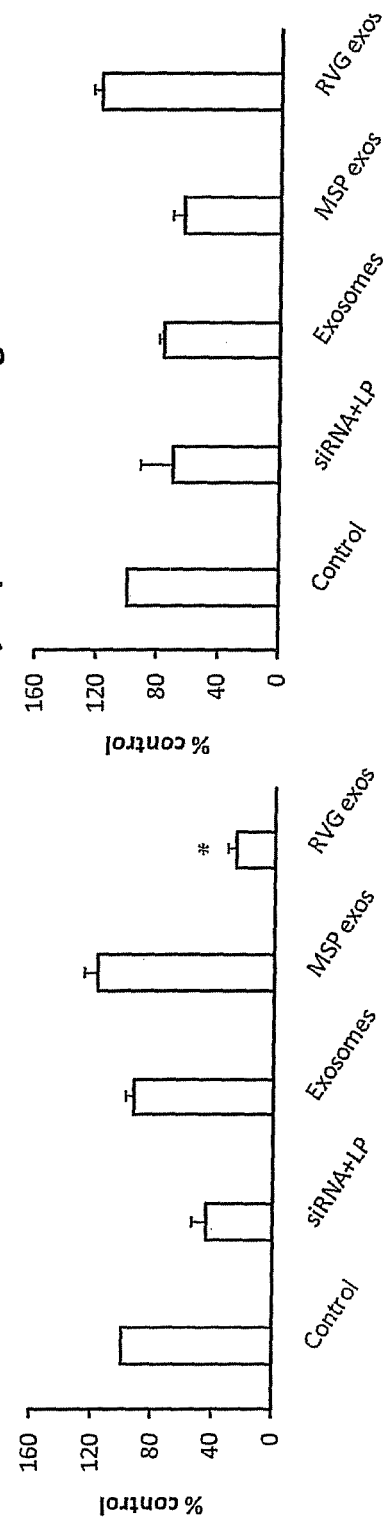

Lamp2b was cloned with cDNA from C2C12 cells and XhoI and BspEI restriction sites were inserted after the signal peptide sequence together with glycine linkers. The full construct was then cloned downstream of the CMV promoter with NheI and HindIII restriction sites into a pEGFP-C1 vector, removing the eGFP in the process. Primers designed to encode RVG [32], MSP [33] and FLAG tag were used to introduce the targeting ligands between XhoI and BspEI at the N-terminus of Lamp2b (FIG. 6A). Primer sequences for the peptides were RVG (YTIWMPENPRPGTPCDIFTNSRGKRASNG) (SEQ ID No: 6):

Forward
(SEQ. ID NO: 7)
5'-tcgatacaccatttggatgcccgagaatccgagaccagggacacctt
gtgacattttaccaatagcagagggaagagagcatccaacgggt-3'

Reverse
(SEQ. ID NO: 8)
5'-ccggacccgttggatgctctcttccctctgctattggtaaaaatgtc
acaaggtgtccctggtctcggattctcgggcatccaaatggtgta-3'

MSP (ASSLNIA) (SEQ ID No: 9):

Forward
(SEQ. ID NO: 10)
5'-tcgagccagcagcctgaacatcgcct-3'

Reverse
(SEQ. ID NO: 11)
5'-ccggaggcgatgttcaggctgctggc-3'

FLAG (DYKDDDDK): (SEQ ID No: 12)

Forward
(SEQ. ID NO: 13)
5'-tcgagattacaaggatgacgatgacaagt-3'

Reverse
(SEQ. ID NO: 14)
5'-ccggacttgtcatcgtcatccttgtaatc-3'

Murine Lysosome-Associated Membrane Glycoprotein 2 (Lamp 2) Isoform 2

Unmodified amino acid sequence
(SEQ ID NO 1)

MCLSPVKGAKLILIFLFLGAVQSNALIVNLTDSKGTCLYAEWEMNFTITYETTNQTN

<-- Signal peptide -->

KTITIAVPDKATHDGSSCGDDRNSAKIMIQFGFAVSWAVNFTKEASHYSIHDIVLSY

NTSDSTVFPGAVAKGVHTVKNPENFKVPLDVIFKCNSVLTYNLTPVVQKYWGIHLQA

FVQNGTVSKNEQVCEEDQTPTT*VAPIIHTTAPSTTTTLTPTSTPTPTPTPTVGNY*

<-- hinge region -->

SIRNGNTTCLLATMGLQLNITEEKVPFIFNINPATTNFTGSCQPQSAQLRLNNSQIK

YLDFIFAVKNEKRFYLKEVNVYMYLANGSAFNISNKNLSFWDAPLGSSYMCNKEQVL

SVSRAFQINTFNLKVQPFNVTKGQYSTAQEC*SLDDDTILIPIIVGAGLSGLIIVIVI*

<-- Transmembrane

*AYLIGRRKTYAGYQTL*

-->

Modified amino acid sequence (added sequence underlined)
MCLSPVKGAKLILIFLFLGAVQSNALIVNLTDSKGTCLY<u>A <peptide tag></u>

<u>GG</u>AEWEMNFTITYETTNQTNKTITIAVPDKATHDGSSCGDDRNSAKIMIQFGFA . . .
("depicts residues 1-39 of SEQ ID NO: 1, followed by peptide tag, and residues 4-91 of SEQ ID NO: 1)

Unmodified nucleotide sequence
(SEQ ID NO: 2)
atgtgcctctctccggttaaaggcgcaaagctcatcctgatctttctgttcctaggagccgttc agtccaatgcattgatagttaatttgacagattcaaagggtacttgcctttatgcagaatggga gatgaatttcacaataacatatgaaactacaaaccaaaccaataaaactataaccattgcagta cctgacaaggcgacacacgatggaagcagttgtggggatgaccggaatagtgccaaaataatga

```
-continued
tacaatttggattcgctgtctcttgggctgtgaattttaccaaggaagcatctcattattcaat tcatgacatcgtgctttcctacaacactagtgatagcacagtatttcctggtgctgtagctaaa ggagttcatactgttaaaaatcctgagaatttcaaagttccattggatgtcatctttaagtgca atagtgttttaacttacaacctgactcctgtcgttcagaaatattggggtattcacctgcaagc ttttgtccaaaatggtacagtgagtaaaaatgaacaagtgtgtgaagaagaccaaactcccacc actgtggcacccatcattcacaccactgccccgtcgactacaactacactcactccaacttcaa cacccactccaactccaactccaaccgttggaaactacagcattagaaatggcaatac tacctgtctgctggctaccatggggctgcagctgaacatcactgaggagaaggtgcctttcatt tttaacatcaaccctgccacaaccaacttcaccggcagctgtcaacctcaaagtgctcaactta ggctgaacaacagccaaattaagtatcttgactttatctttgctgtgaaaaatgaaaaacggtt ctatctgaaggaagtgaatgtctacatgtatttggctaatggctcagctttcaacatttccaac aagaacctagcttctgggatgccctctgggaagttcttatatgtgcaacaaagagcaggtgc tttctgtgtctagagcgtttcagatcaacaccctttaacctaaaggtgcaacctttaatgtgac aaaaggacagtattctacagcccaggagtgttcgctggatgatgacaccattctaataccaatt atagttggtgctggtctttcaggcttgattatcgttatagtgattgcttacctaattggcagaa gaaagacctatgctggatatcagactctgtaa Modified nucleotide sequence (added sequence in italics and restrictions
sites used for cloning in underlined)
                                                        (DEQ ID NO: 25)
atgtgcctctctccggttaaaggcgcaaagctcatcctgatctttctgttcctaggagccgttc agtccaatgcattgatagttaatttgacagattcaaagggtacttgcctttat*GCTCGAGGTCA*

*CATCCGGAGGT*gcagaatgggagatgaatttcacaataacatatgaaactacaaaccaaaccaa taaaactataaccattgcagtacctgacaaggcgacacacgatggaagcagtt . . .
```

Transfection

Transfection of dendritic cells was performed with 5 μg of pEGFP-NAD or pLamp2b derivatives and 5 μl of TransIT LT1 transfection reagent (Minis Bio) in a 6-well plate with $10^6$ cells on Day 4 after harvesting and isolation of exosomes is done on Day 8.

Reverse Transcription qPCR

Reverse transcription was performed with 500 ng of RNA and random primer using Precision Reverse Transcription Kit (Primer Design) as per manufacturer's instruction. qPCR experiments were performed on an ABI7000 thermal cycler in 20 μl reactions, with 0.5 nM of each primer and 2 μl of each cDNA preparation, using Precision qPCR Mastermix (Primer Design) as per manufacturer's instructions.

```
qPCR primer sequences
Cyclophilin-B human
                                       (SEQ ID NO: 15)
Forward 5'-AAAGTCACCGTCAAGGTGTATTT-3'

(SEQ ID NO: 16)
Reverse 5'-TCACCGTAGATGCTCTTTCCTC-3'

GAPDH human
                                       (SEQ ID NO: 17)
Forward 5'-AAGGTGAAGGTCGGAGTCAA-3'

(SEQ ID NO: 18)
Reverse 5'-GAAGATGGTGATGGGATTTC-3'

GAPDH mouse
                                       (SEQ ID NO: 19)
Forward 5'-CAATGTGTCCGTCGTGGATCT-3'

(SEQ ID NO: 20)
Reverse 5'-TAGCCCAAGATGCCCTTCAGT-3' eGFP
                                       (SEQ ID NO: 21)
Forward 5'-TCTTCAAGTCCGCCATGCC-3'

(SEQ ID NO: 22)
Reverse 5'-TGTCGCCCTCGAACTTCAC-3'

18S
                                       (SEQ ID NO: 23)
Forward 5'-GTAACCCGTTGAACCCCATT-3'

(SEQ ID NO: 24)
Reverse 5'-CCATCCAATCGGTAGTAGCG-3'
```

Mouse cyclophilin B: Mm_PPIB_1_SG_Quantitect Primer Assay (Qiagen)

Western Blotting

Cell samples and exosomes were lysed in a 10 mM Tris pH 7.4 buffer containing 0.1% SDS, a protease inhibitor cocktail and DNase. Samples were separated on NuPAGE® Novex 4-12% Bis-Tris Gel (Invitrogen), and transferred to a PVDF membrane (Amersham Biosciences). The membrane was then blocked with 10% milk in PBS for 1 hour, incubated with primary antibody for 90 min at a dilution of 1:5000 for anti-Lamp2 antibody (Abcam), 1:10000 for anti-GAPDH (Abcam) and anti-cyclophilin B (Abcam). Membranes were incubated with HRP-conjugated secondary antibody 1:5000 dilution for 45 minutes at room temperature before film exposure. All steps were followed by 3 washes with PBST for 10 min each.

Transfection and Electroporation with Exosomes and DNase Protection Assay

1 µg of the pEGFP-NAD plasmid was mixed with 1 µl of the transfection reagent, 3 of exosomes and topped up to 100 µl with DMEM. The solution was incubated for 3 hours at 37° C. and then subjected to DNase treatment for 10 minutes at 37° C. with the addition of 1 µl of RQ DNase I (Promega) and 10 µl of RQ DNase buffer. The DNase was inactivated by 10 µl of STOP buffer (Promega) before the direct addition of the entire solution to Neuro2A cells in a 24-well format.

Exosomes were loaded to a protein concentration of 6 µg in 200 µl of electroporation buffer (1.15 mM potassium phosphate pH 7.2, 25 mM KCl, 21% Optiprep) and 2 µg of pEGFP-NAD or 100 pmol of cyclophilin siRNA was added, mixed and electroporated in a 4 mm cuvette. For the DNase protection Assay, 20 µl of the electroporated solution was added to 70 µl of distilled water, 10 µl of RQ DNase Buffer and 1 µl RQ DNase I (Promega) and incubated at 37° C. for 10 min before inhibiting the reaction with 10 µl of STOP buffer. 10 µl of each sample was run on each lane in a 0.8% agarose TAE gel.

Transfection of Cells with Exosomes 100 ul (electroporation) or the entire mixture (transfection) was added to Neuro2A cells in complete medium. For siRNAs, the medium is changed after 24 hours. The cells were harvested 48 hours after addition of the exosomes.

Exosome Pulldown Assay

20 µl of Protein-A Sepharose beads (Sigma P9424) were incubated overnight at 4° C. in 500 µl PBS and 2 mg/ml BSA. In the protocol, beads were pelleted during the steps by centrifugation at 100 g for 2 minutes at 4° C. The beads were subsequently washed 3 times with 1 ml PBS for 5 minutes each wash. 1 µl Rabbit anti-FLAG (Sigma F2555) or 1 µl of Rabbit anti-Ago1 (Upstate 07-599) was loaded onto the beads in 100 µl of PBS with 2 mg/ml BSA for 4 hours at 4° C. and the beads were subsequently washed 3 times as described above. Normal exosomes and FLAG-exosomes were spun at 200 g for 10 min to remove contaminating debris and added to the beads to a protein concentration of 10 µg/ml in 200 µl of PBS. After incubation, the beads were subsequently washed 3 times as described above, then eluted in 0.1% SDS and the entire supernatant was loaded onto a polyacrylamide gel. A Western blot against Lamp-1, an exosomal protein was used to detect the presence of exosomes pulled down by the antibodies.

Statistics

All experiments, unless otherwise stated, were all performed in triplicates. All error bars used in this report are standard deviations. Statistical analyses of the data were performed using SPSS program 16.0 by using the non-parametric Krusckal Wallis test followed by the Mann-Whitney U test.

Exosome-Mediated Targeted Systemic Delivery of siRNA to the Brain

Figure 9A:
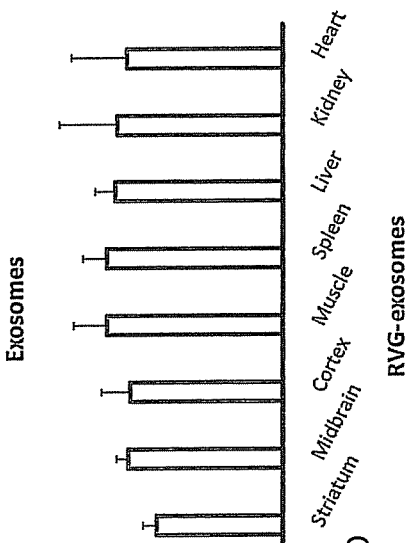
FIGS. 9A-9J. In vivo delivery of siRNA with targeted exosomes results in CNS-specific gene knockdown.
Figure 9B:
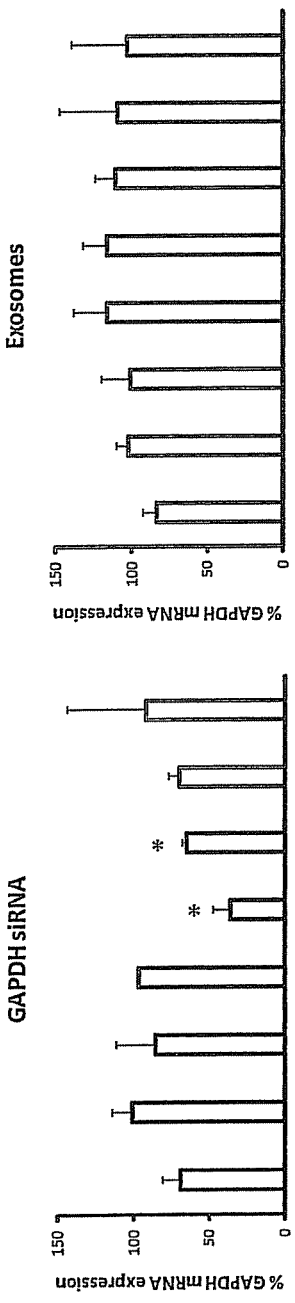
Figure 9C:
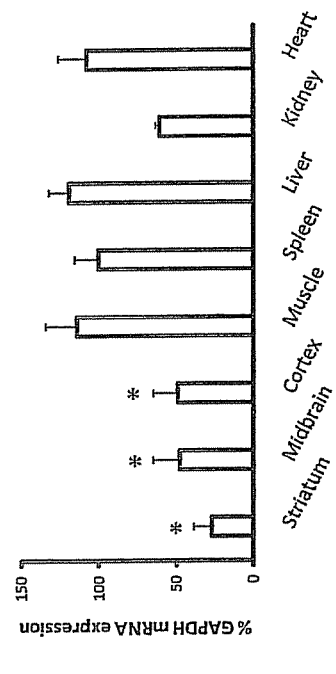
Figure 9D:
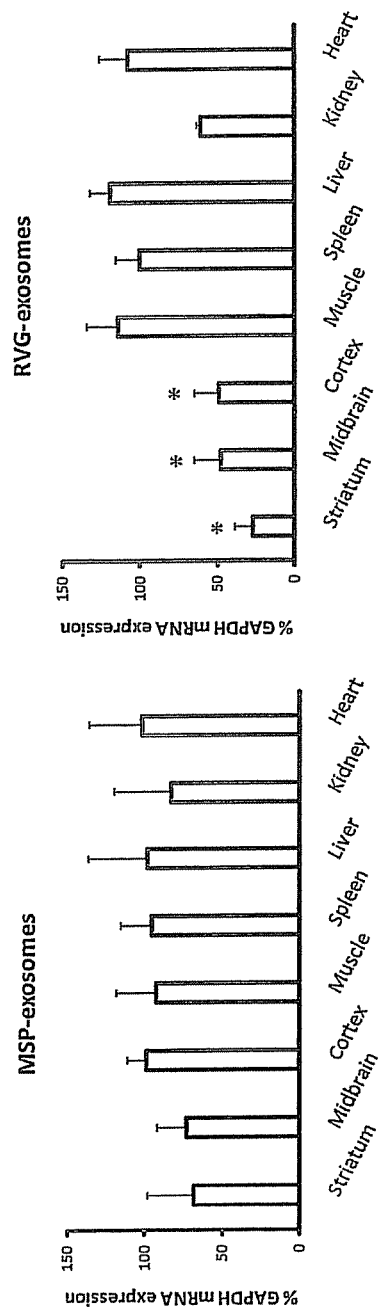

Immunologically inert exosomes were harvested from murine bone marrow-derived dendritic cells and targeting moieties—muscle-specific peptide (MSP) and neuron-specific rabies viral glycoprotein (RVG), were genetically engineered onto Lamp2b, an exosomal membrane protein, to alter tissue specificity of these exosomes, as described above. To investigate the potential for exosome-mediated systemic siRNA delivery in vivo and characterize the tissue distribution, the ubiquitously highly-expressed housekeeping GAPDH gene was chosen as a target. We electroporated 150 µg of optimized GAPDH siRNA with 150 µg of either unmodified, RVG- or MSP-exosomes, then purified the exosomes by ultracentrifugation and removed unencapsulated siRNA in the supernatant. Exosomes were resuspended in 80 µl of 5% glucose before intravenous injection in C57BL/6 mice. Injection of naked siRNA (150 µg) resulted in detectable GAPDH silencing in the spleen, liver and kidney, corresponding to reported siRNA sequestration after tail vein delivery [42] (FIG. 9A). In contrast, exosome-encapsulated siRNAs appeared to have no natural affinity to these organs and were resistant to non-specific uptake. Systemic administration of unmodified exosomes did not induce GAPDH silencing in any organ analyzed (FIG. 9b). Injection of MSP-exosomes produced a slight, but non-significant GAPDH silencing in brain and kidney (FIG. 9C), whereas injection of RVG-exosomes resulted in significant knockdown of GAPDH mRNA in several brain regions (FIG. 9D), a tissue expressing the target of RVG ligand-nicotinic acetylcholine receptors [32]. We also observed a non-significant decrease of GAPDH mRNA level in kidney 3 days after injection. Although in vivo tissue specificity was not seen with MSP-exosomes, the relatively weak targeting capabilities of MSP [43] and the abundance of muscle tissue may have resulted in much lower average siRNA concentration within muscle cells and hence, correspondingly lower gene knockdown.

Figure 9E:
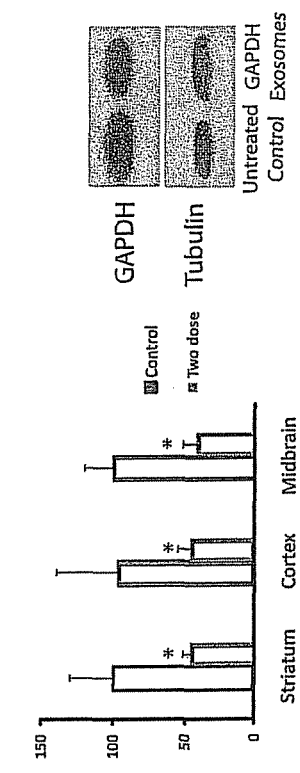
Figure 9F:
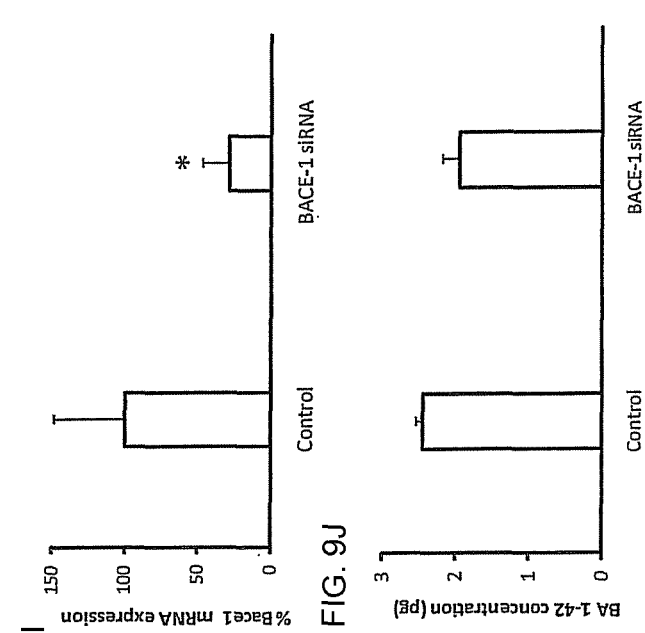
Figure 9G:
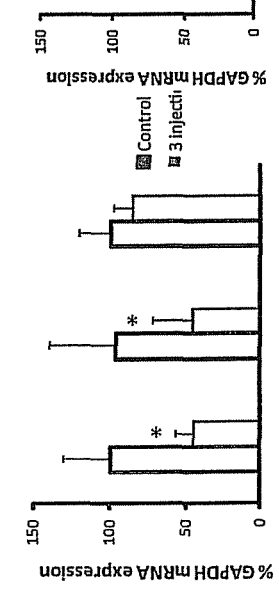

We next investigated if re-administration of exosomes leads to decreased transgene delivery efficiency previously described in viruses [44, 45] and liposomes. We designed two different experiments to assess this question. First, we studied if pre-innoculating the animals with empty RVG-exosomes would reduce the efficacy of delivery. The animals were injected with empty RVG-exosomes at the same dose 3 and 2 weeks before injection of electroporated RVG-exosomes containing GAPDH siRNA. The animals were then sacrificed 3 days later and brain GAPDH knockdown was assessed. Results indicated a minimal decrease in silencing efficacy between unprimed and primed mice (FIGS. 9D and 9E), demonstrating that targeted exosomes can be readministered multiple times without loss in delivery efficacy. Finally, to confirm the results, we injected three mice with two doses of RVG-exosomes containing GAPDH siRNA at the same concentration. Animals were injected 7 and 3 days before harvesting the tissues and GAPDH mRNA and protein knockdown were assessed in the brain. Knockdown was observed with GAPDH mRNA (50.2%±9.1%, p<0.05) and protein levels (19.6%±2.3%, not significant) in the cortex (FIGS. 9F and 9G). These experiments validated the previous results and demonstrated that RVG-exosomes can be re-administered multiple times without loss of delivery efficacy allowing for long-term target silencing.

Figure 9H:
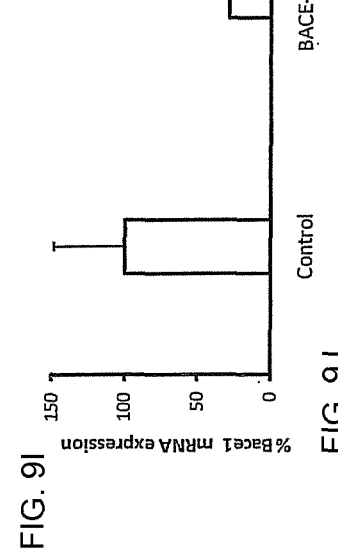
Figure 9I:
Figure 9J:
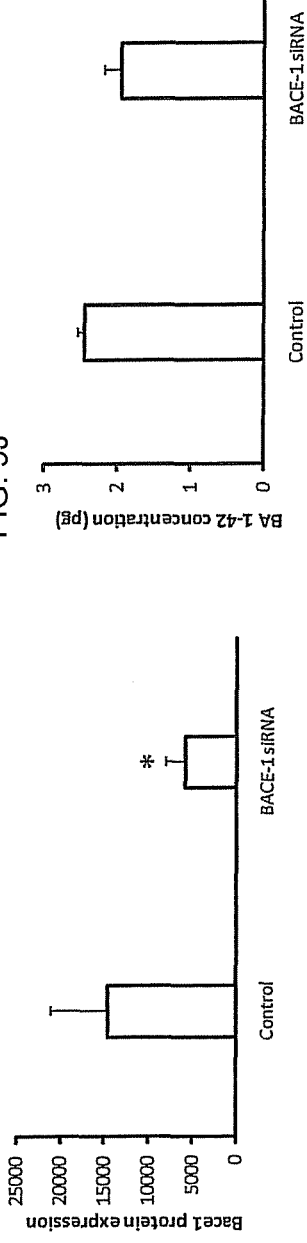

Given the success of knockdown with GAPDH, BACE-1, a key enzyme in the pathogenesis of Alzheimer's disease (AD), was targeted to evaluate the therapeutic potential of this technology. Previous studies in transgenic APP over-expressing [46, 47] and normal [48] mice suggested that BACE-1 is a strong candidate for anti-AD therapeutic intervention. We delivered two BACE-1 siRNAs, previously validated in vitro, to normal C57BL/6 mice. 150 µg of RVG-exosomes and 150 µg of each BACE-1 siRNA were electroporated, purified and resuspended in 5% glucose before delivery. Significant mRNA (72%±18%) and protein (60%±13%) knockdown in cortex 3 days after administration (FIGS. 9H and 9I). Moreover we demonstrated a decrease of 20% in the total content of β-amyloid 1-42, a main component of the amyloid plaques in the Alzheimer's pathology (FIG. 9J). This result was comparable to the β-amyloid 1-40 decrease demonstrated in normal mice after intraventricular injection of BACE-1 inhibitors [48]. This experiment demonstrated the therapeutic potential of this technology, which is potentially ideally suited for long-term silencing of genes related with neurodegenerative diseases.

[1] Smith A J, Schlichtenbrede F C, Tschernutter M, Bainbridge J W, Thrasher A J, Ali R R (2003), AAV-Mediated gene transfer slows photoreceptor loss in the RCS rat model of retinitis pigmentosa, Mol Ther 8(2):188-95.

[2] Ely A, Naidoo T, Mufamadi S, Crowther C, Arbuthnot P (2008), Expressed anti-HBV primary microRNA shuttles inhibit viral replication efficiently in vitro and in vivo, Mol Ther 16(6):1105-12.

[3] White M D, Farmer M, Mirabile I, Brandner S, Collinge J, Mallucci G R (2008), Single treatment with RNAi against prion protein rescues early neuronal dysfunction and prolongs survival in mice with prion disease, Proc Natl Acad Sci USA 105(29):10238-43.

[4] Reynolds A, Leake D, Boese Q, Scaringe S, Marshall W S, Khvorova A (2004), Rational siRNA design for RNA interference, Nat Biotechnol 22(3):326-30.

[5] Takakura Y, Nishikawa M, Yamashita F, Hashida M (2001), Development of gene drug delivery systems based on pharmacokinetic studies, Eur J Pharm Sci 13(1):71-76.

[6] Kawabata K, Takakura Y, Hashida M (1995), The fate of plasmid DNA after intravenous injection in mice: involvement of scavenger receptors in its hepatic uptake, Pharm Res 12(6):825-30.

www.wiley.co.uk/genmed/clinical/Retrieved on 9 Sep. 2008.

[8] Lowenstein P R, Mandel R J, Xiong W D, Kroeger K, Castro M G (2007), Immune responses to adenovirus and adeno-associated vectors used for gene therapy of brain diseases: the role of immunological synapses in understanding the cell biology of neuroimmune interactions, Curr Gene Ther 7(5):347-60.

[9] Alexander I E, Cunningham S C, Logan G J, Christodoulou J (2008), Potential of AAV vectors in the treatment of metabolic disease, Gene Ther.;15(11):831-9.

[10] Hasbrouck N C, High K A (2008), AAV-mediated gene transfer for the treatment of hemophilia B: problems and prospects, Gene Ther 15(11):870-5.

[11] Daniel R, Smith J A (2008), Integration site selection by retroviral vectors: molecular mechanism and clinical consequences, Hum Gene Ther 19(6):557-68.

[12] Zhang J S, Liu F, Huang L (2005), Implications of pharmacokinetic behavior of lipoplex for its inflammatory toxicity, Adv Drug Deliv Rev 57(5):689-98.

[13] Ishida T, Masuda K, Ichikawa T, Ichihara M, Irimura K, Kiwada H (2005), Accelerated clearance of a second injection of PEGylated liposomes in mice, Int J Pharm 255:167-74.

[14] Ishida T, Ichihara M, Wang X, Yamamoto K, Kimura J, Majima E, Kiwada H. (2006), Injection of PEGylated liposomes in rats elicits PEG-specific IgM, which is responsible for rapid elimination of a second dose of PEGylated liposomes, J Control Release 112:15-25.

[15] Ishida T, Ichihara M, Wang X, Yamamoto K, Kimura J, Majima E, Kiwada H (2006), Injection of PEGylated liposomes in rats elicits PEG-specific IgM, which is responsible for rapid elimination of a second dose of PEGylated liposomes, J Control Release 112:15-25.

[16] Jiang H, Couto L B, Patarroyo-White S, Liu T, Nagy D, Vargas J A, et al (2006), Effects of transient immunosupression on adenoassociated, virus-mediated, liver-directed gene transfer in rhesus macaques and implications for human gene therapy, Blood 108(10):3321-8.

[17] Wang Z, Kuhr C S, Allen J M, Blankinship M, Gregorevic P, Chamberlain J S, et al (2007), Sustained AAV-mediated dystrophin expression in a canine model of Duchenne muscular dystrophy with a brief course of immunosuppression, Mol Ther 15(6):1160-6.

[18] Li J Z, Li H, Hankins G R, Dunford B, Helm G A (2005), Local immunomodulation with CD4 and CD8 antibodies, but not cyclosporine A, improves osteogenesis induced by ADhBMP9 gene therapy, Gene Ther 12(16):1235-41.

[19] Zaiss A K, Muruve D A (2005), Immune responses to adeno-associated viral vectors, Curr Gene Ther 5(3):323-31.

[20] Taylor N, Uribe L, Smith S, Jahn T, Kohn D B, Weinberg K (1996), Correction of interleukin-2 receptor function in X-SCID lymphoblastoid cells by retrovirally mediated transfer of the gamma-c gene, Blood 87(8):3103-7.

[21] Oh Y K, Sohn T, Park J S, Kang M J, Choi H G, Kim J A, et al (2004), Enhanced mucosal and systemic immunogenicity of human papillomavirus-like particles encapsidating interleukin-2 gene adjuvant, Virology 328 (2):266-73.

[22] Williams D A (2007), RAC reviews serious adverse event associated with AAV therapy trial, Mol Ther 15(12):2053-4.

[23] Raposo G, Nijman H W, Stoorvogel W, Liejendekker R, Harding C V, Melief D J Geuze H J (1996), B lymphocytes secrete antigen-presenting vesicles, J Exp Med 183:1161-1172.

[24] Zitvogel L, Regnault A, Lozier A, Wolfers J, Flament C, Tenza D, Ricciardi-Castagnoli P, Raposo G, Amigorena S (1998), Eradication of established murine tumors using a novel cell-free vaccine: dendritic cell-derived exosomes, Nat Med 4:594-600.

[25] Hao S, Moyana T, Xiang J (2007), Review: cancer immunotherapy by exosome-based vaccines, Cancer Biother Radiopharm 22:692-703.

[26] Valadi H, Ekström K, Bossios A, Sjöstrand M, Lee J J, Lötvall JO (2007), Exosome-mediated transfer of mRNAs and microRNAs is a novel mechanism of genetic exchange between cells, Nat Cell Biol 9(6):654-9.

[27] Skog J, Würdinger T, van Rijn S, Meijer D H, Gainche L, Sena-Esteves M, Curry W T Jr, Carter B S, Krichevsky A M, Breakefield X O (2008), Glioblastoma microvesicles transport RNA and proteins that promote tumour growth and provide diagnostic biomarkers, Nat Cell Biol 10(12):1470-6.

[28] Quah B J, O'Neill H C (2005), The immunogenicity of dendritic cell-derived exosomes, Blood Cells Mol Dis 35:94-110.

[29] Théry C, Zitvogel L, Amigorena S (2002), Exosomes: composition, biogenesis and function, Nat Rev Immunol 2(8):569-79.

[30] Jooss K, Yang Y, Fisher K J, Wilson J M (1998), Transduction of dendritic cells by DNA viral vectors directs the immune response to transgene products in muscle fibers, J Virol 72(5):4212-23.

[31] Reis e Sousa C (2006), Dendritic cells in a mature age, Nat Rev Immunol 6(6):476-83.

[32] Kumar P, Wu H, McBride J L, Jung K E, Kim M H, Davidson B L, Lee S K, Shankar P, Manjunath N (2007), Transvascular delivery of small interfering RNA to the central nervous system, Nature 448(7149):39-43.

[33] Flint P W, Li Z B, Lehar M, Saito K, Pai S I (2005), Laryngeal muscle surface receptors identified using random phage library, Laryngoscope 115(11):1930-7.

34 Rippe K, Mücke N, Langowski J (1997), Superhelix dimensions of a 1868 base pair plasmid determined by scanning force microscopy in air and in aqueous solution, *Nucleic Acids Res* 25(9):1736-44.

35 Vijayanathan V, Thomas T, Shirahata A, Thomas T J (2001), DNA condensation by polyamines: a laser light scattering study of structural effects, *Biochemistry* 40(45): 13644-51.

36 Lentz, T. L. Rabies virus binding to an acetylcholine receptor alpha-subunit peptide (1990). J. Mol. Recognit. 3, 82-88.

37 Zeng J, Too H P, Ma Y, Luo E S E, Wang S. A synthetic peptide containing loop 4 of nerve growth factor for targeted gene delivery (2004). *J Gene Med.;* 6:1247-1256.

38 McKay T, Reynolds P, Jezzard S, Curiel D, Coutelle C. Secretin-mediated gene delivery, a specific targeting mechanism with potential for treatment of biliary and pancreatic disease in cystic fibrosis (2002). *Mol Ther;* 5:447-454.

39 C. Théry, S. Amigorena, G. Raposo, A. Clayton, Isolation and characterization of exosomes from cell culture supernatants and biological fluids. *Curr Protoc Cell Biol Ed.* (Wiley, New York, April 2006) Chapter 3, Unit 3.22 (2006).

40 V. R. Simhadri, K. S. Reiners, H. P. Hansen, D. Topolar, V. L. Simhadri et al., Dendritic cells release HLA-B-associated transcript-3 positive exosomes to regulate natural killer function. *PLoS One.* 3(10), e3377 (2008), doi:10.1371/journal.pone.0003377.

41 Y. C. Wang, X. B. Hu, F. He, F. Feng, L. Wang et al., Lipopolysaccharide-induced maturation of bone marrow-derived dendritic cells is regulated by notch signaling through the up-regulation of CXCR4. *J Biol Chem.* 284 (23), 15993-6003 (2009).

42 S. D. Larson, L. N. Jackson, L. A. Chen, P. G. Rychahou, B. M. Evers, Effectiveness of siRNA uptake in target tissues by various delivery methods. *Surgery.* 142(2): 262-9 (2007).

43 H. Yin, H. M. Moulton, C. Betts, Y. Seow, J. Boutilier et al., A fusion peptide directs enhanced systemic dystrophin exon skipping and functional restoration in dystrophin-deficient mdx mice. *Hum Mol Genet.* 18(22):4405-14 (2009).

44 F. A. Nunes, E. E. Furth, J. M. Wilson, S. E. Raper, Gene transfer into the liver of nonhuman primates with El-deleted recombinant adenoviral vectors: safety of readministration. *Hum Gene Ther.* 10(15), 2515-26 (1999).

45 S. C. Gonzalez, M. M. McMenamin, H M Charlton, J. Goodman, T Lantos, Readministration of adenoviral gene delivery to dopamine neurons. *Neuroreport.* 18(15), 1609-14 (2007).

46 F. M. Laird, H. Cai, A. V. Savonenko A. V. M. H. Farah, K. He et al., BACE1, a major determinant of selective vulnerability of the brain to amyloid-beta amyloidogenesis, is essential for cognitive, emotional, and synaptic functions. *J. Neurosci.* 25(50), 11693-11709 (2005).

47 O. Singer, R. A. Man, E. Rockenstein, L. Crews, N. G. Coufal et al., Targeting BACE1 with siRNAs ameliorates Alzheimer disease neuropathology in a transgenic model. *Nat. Neurosci.* 8(10), 1343-1349 (2005).

48 K. Nishitomi, G. Sakaguchi, Y. Horikoshi, A. J. Gray, M. Maeda et al., BACE1 inhibition reduces endogenous Abeta and alters APP processing in wild-type mice. *J. Neurochem.* 99(6), 1555-63 (2006).

---

What is claimed is:

1. A method of targeting an exosome to a selected tissue or cell type, comprising expressing a targeting moiety as a fusion protein between the targeting moiety and an exosomal transmembrane protein on the surface of the exosome, wherein the targeting moiety is a peptide of from 5 to 100 amino acids in length, and binds a cell surface moiety expressed on the surface of the selected tissue or cell type, wherein the exosomal transmembrane protein is selected from Lamp-1, Lamp-2, CD13, Flotillin, Syntaxin-3, CD44, ICAM-1, Integrin alpha4, L1CAM, LFA-1, Vti-1A and B, CD9, CD37, CD53, CD63, CD81, CD82 and tetraspanins.

2. The method according to claim 1, wherein the targeting moiety targets the exosome to tissue or cells selected from muscle, brain, liver pancreas and/or lung.

3. The method according to claim 1, wherein the targeting moiety targets the exosome to diseased tissue or diseased cells.

4. The method according to claim 1, wherein the targeting moiety is separated from the transmembrane protein by a spacer or linker sequence.

5. The method according to claim 4, wherein the spacer or linker sequence is a peptide of from 1 to 5 amino acids.

6. The method according to claim 5, wherein the spacer or linker comprises alanine, arginine, serine and/or glycine residues.

7. The method according to claim 1, wherein the exosome is loaded with exogenous genetic material.

8. The method according to claim 3, wherein the diseased tissue is a tumour tissue, or the diseased cell is a tumour cell.

* * * * *